US005612377A

United States Patent [19]

Crooks et al.

[11] Patent Number: 5,612,377
[45] Date of Patent: Mar. 18, 1997

[54] METHOD OF INHIBITING LEUKOTRIENE BIOSYNTHESIS

[75] Inventors: Stephen L. Crooks, Mahtomedi, Minn.;
Bryon A. Merrill, River Falls, Wis.;
Paul D. Wightman, Woodbury, Minn.

[73] Assignee: Minnesota Mining and Manufacturing Company, St. Paul, Minn.

[21] Appl. No.: 455,643

[22] Filed: May 31, 1995

Related U.S. Application Data

[63] Continuation-in-part of Ser. No. 286,017, Aug. 4, 1994, abandoned.

[51] Int. Cl.$^6$ ........................................ A01N 47/28
[52] U.S. Cl. ........................ 514/596; 514/597; 514/598
[58] Field of Search .............................. 514/210, 592, 514/596, 597, 598

[56] References Cited

U.S. PATENT DOCUMENTS

| | | | |
|---|---|---|---|
| 3,505,454 | 4/1970 | Krenzer | 424/272 |
| 3,528,949 | 9/1970 | Rutledge | 528/367 |
| 3,900,484 | 8/1975 | Chupp | 260/301 |
| 4,108,993 | 8/1978 | Bonne et al. | 424/248.57 |
| 4,260,411 | 4/1981 | Yoshida et al. | 514/596 |
| 4,623,662 | 11/1986 | De Vries | 514/596 |
| 4,728,670 | 3/1988 | Haslanger et al. | 514/484 |
| 4,769,387 | 9/1988 | Summers et al. | 514/468 |
| 4,822,809 | 4/1989 | Summers et al. | 514/367 |
| 4,822,811 | 4/1989 | Summers | 514/411 |
| 4,873,259 | 10/1989 | Summers, Jr. et al. | 514/443 |
| 4,981,865 | 1/1991 | Belliotti et al. | 514/480 |
| 4,992,464 | 2/1991 | Brooks et al. | 514/443 |
| 5,036,067 | 7/1991 | Girard et al. | 514/224.8 |
| 5,066,658 | 11/1991 | Demers et al. | 514/269 |
| 5,179,106 | 1/1993 | Mohrs et al. | 514/311 |
| 5,185,363 | 2/1993 | Brooks et al. | 514/438 |
| 5,326,787 | 7/1994 | Brooks et al. | 514/507 |
| 5,407,959 | 4/1995 | Dellaria et al. | 514/598 |

FOREIGN PATENT DOCUMENTS

| | | |
|---|---|---|
| 196184 | 10/1986 | European Pat. Off. . |
| 279281 | 8/1988 | European Pat. Off. . |
| 292699 | 11/1988 | European Pat. Off. . |
| 320628 | 6/1989 | European Pat. Off. . |
| 374602 | 6/1990 | European Pat. Off. . |
| 408760 | 1/1991 | European Pat. Off. . |
| 412939 | 2/1991 | European Pat. Off. . |
| 56-53646 | 5/1981 | Japan . |
| 89/04299 | 5/1989 | WIPO . |
| 90/08545 | 8/1990 | WIPO . |
| 90/12008 | 10/1990 | WIPO . |
| 91/14674 | 10/1991 | WIPO . |
| 92/12141 | 7/1992 | WIPO . |
| 94/06790 | 3/1994 | WIPO . |

OTHER PUBLICATIONS

*Biochem. J.* (1991) 274, 287–292 (Riendeau et al.).
*Biochem. Cell Biol.* (1992) 70, 228–236 (Falgueyret et al.).
*J. Med. Chem.* (1993) 36, 3580–3594 (Satoh et al.).

*Primary Examiner*—Peter F. Kulkosky
*Attorney, Agent, or Firm*—Gary L. Griswold; Walter N. Kirn; Ted K. Ringsred

[57] ABSTRACT

A method of inhibiting leukotriene biosynthesis, involving administering a compound of the formula:

$$\text{MO}-\underset{R}{\text{N}}-\overset{O}{\underset{}{\text{C}}}-\underset{R''}{\text{N}}-\text{Ar}(R')_n$$

wherein M, R, R', R", and n are as defined herein. Also, a pharmaceutical composition involving such a compound and the use of such compounds in the manufacture of a pharmaceutical composition for inhibiting leukotriene biosynthesis.

30 Claims, No Drawings

METHOD OF INHIBITING LEUKOTRIENE BIOSYNTHESIS

This application is a continuation-in-part of application Ser. No. 08/286,017, filed Aug. 4, 1994, incorporated herein by reference, now abandoned.

BACKGROUND OF THE INVENTION

1. Field of the Invention

This invention relates to methods of inhibiting leukotriene biosynthesis. In another aspect this invention relates to methods of treating diseases mediated by leukotrienes. In yet another aspect this invention relates to pharmaceutical compositions for inhibiting leukotriene biosynthesis.

2. Description of the Related Art

Arachidonic acid, a component of phospholipids found in cell membranes, is metabolized through an array of enzymatic pathways to afford biologically active metabolites including the leukotrienes. The leukotrienes are very potent substances, producing a variety of biological effects when present in the nanomolar or picomolar concentration range. They have been implicated in a variety of disease states. For example, Leukotriene $C_4$ and Leukotriene $D_4$ are potent constrictors of human airway smooth muscle. Aerosol administration of these substances to nonasthmatic volunteers induces bronchoconstriction. Leukotriene $B_4$ is a potent chemotactic factor for inflammatory cells such as polymorphonuclear leukocytes. Leukotriene $B_4$ has been found in the synovial fluids of rheumatoid arthritis patients and in psoriatic lesions. Leukotrienes have also been implicated as important mediators in allergic rhinitis, adult respiratory distress syndrome, inflammatory bowel disease, ischemic induced myocardial injury, reperfusion injury, gout, asthma, psoriasis, stroke, spinal cord injury and traumatic brain injury.

SUMMARY OF THE INVENTION

This invention provides a method of inhibiting leukotriene biosynthesis in an animal and of treating in an animal a condition responsive to such inhibition, comprising administering to the animal, in an amount effective to inhibit leukotriene biosynthesis, a compound of Formula I:

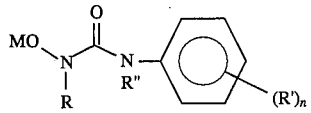

Formula I wherein n is 0, 1, 2 or 3,

R is selected from the group consisting of hydrogen; cyclic alkyl containing five to ten carbon atoms; straight chain or branched chain alkyl containing one to fourteen carbon atoms and substituted straight chain or branched chain alkyl containing one to twelve carbon atoms, wherein the substituent is alkoxycarbonyl wherein the alkoxy group contains one to four carbon atoms; alkoxyalkyl wherein the alkoxy moiety contains one to six carbon atoms and the alkyl moiety contains one to six atoms;

each R' is independently selected from the group consisting of halogen; nitro; straight chain or branched chain alkyl containing one to five carbon atoms; alkoxy containing one to four carbon atoms; alkoxyphenyl wherein the alkoxy group contains one to eight carbon atoms; alkylthio containing one to four carbon atoms; alkylsulfonoxy containing one to four carbon atoms; alkylsulfinyl containing one to four carbon atoms; alkylsulfonyl containing one to four carbon atoms; benzoyl; benzyl; cyclohexylmethoxy; cyclopentyloxy; phenoxy; phenyl; phenylalkyloxy wherein the alkyl group contains one to four carbon atoms; trifluoromethyl; trifluoromethylthio; and trifluoromethylsulfonoxy;

R" is selected from the group consisting of hydrogen and straight chain alkyl containing one to twelve carbon atoms; and M is selected from the group consisting of hydrogen, a pharmaceutically acceptable cation, and a pharmaceutically acceptable metabolically cleavable group with the proviso that R, R', and R" are not all hydrogen.

This invention also provides a pharmaceutical composition for the treatment of an animal having a condition responsive to treatment by inhibition of leukotriene biosynthesis, comprising (i) a pharmaceutically acceptable vehicle, and (ii) a compound of Formula I where n, R, R', R", and M are as defined above in an amount effective to inhibit leukotriene biosynthesis.

This invention also provides for the use of a compound of Formula I in the manufacture of a pharmaceutical composition for use in inhibiting leukotriene biosynthesis.

DETAILED DESCRIPTION OF THE INVENTION

The method of this invention comprises administering a compound of Formula I:

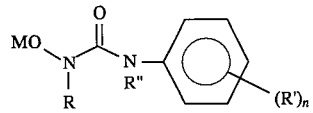

Formula I

The R substituent is defined above. Preferred R substituents include straight chain or branched chain alkyl containing one to six carbon atoms and cycloalkyl containing five to eight carbon atoms. When R is alkyl as defined above, preferred R substituents include methyl, 1-methylethyl, 1-ethylpropyl, and 1-methylpropyl.

Preferred R' substituents include halogen, nitro, straight chain alkyl containing one to four carbon atoms, alkylthio containing one to four carbon atoms and phenoxy. When R' is alkylthio as defined above, the preferred R' substituent is thiomethyl.

Preferred R" substituents include hydrogen and methyl.

In Formula I, n is 0, 1, 2 or 3, preferably 0 or 1. When n is 1, R' may be in the ortho, meta or para position, preferably the para position, on the phenyl ring.

The M substituent is selected from the group consisting of hydrogen, a pharmaceutically acceptable cation, and a pharmaceutically acceptable metabolically cleavable group.

The term "pharmaceutically acceptable cation" refers to nontoxic cations well known to those skilled in the art and including but not limited to those based on the alkali and alkaline earth metals such as sodium, lithium, potassium, magnesium, aluminum and the like, as well as nontoxic ammonium, quaternary ammonium, and amine cations, derived from nitrogenous bases of sufficient basicity to form salts with the N-hydroxy group of the compounds of Formula I (where M is hydrogen).

The term "metabolically cleavable group" denotes a moiety that is readily cleaved in vivo from the compound bearing it. The compound after cleavage remains or becomes pharmacologically active. Metabolically cleavable groups generally are derived from compounds (well known to those skilled in the art) reactive with the N-hydroxy group of compound of Formula I where M is hydrogen. Such groups include, but are not limited to, alkanoyl (such as acetyl, propionyl and the like), unsubstituted and substituted aroyl (such as benzoyl and substituted benzoyl), alkoxycarbonyl (such as ethoxycarbonyl), monoesters formed with dicarboxylic acids (such as succinyl), and the like. Compounds bearing metabolically cleavable groups act as prodrugs and may exhibit improved bioavailability over the parent compound.

M is preferably hydrogen.

Preferred compounds for use in the method of this invention include:

1-hydroxy-1-methyl-3-[3-(trifluoromethylsulfonoxy)phenyl]urea,
1-hydroxy-1-methyl-3-[3-(methylthio)phenyl]urea,
1-hydroxy-1-methyl-3-[3-(trifluoromethylthio)phenyl]urea,
1-hydroxy-3-(3-methoxyphenyl)-1-methylurea,
3-(3-bromophenyl)-1-hydroxy-1-methylurea,
1-hydroxy-1-methyl-3-(3-methylphenyl)urea,
3-(3-fluorophenyl)-1-hydroxy-1-methylurea,
1-hydroxy-1-methyl-3-(3-nitrophenyl)urea,
1-hydroxy-1-methyl-3-phenylurea,
3-(4-fluorophenyl)-1-hydroxy-1-methylurea,
3-(4obutylphenyl)-1-hydroxy-1-methylurea,
1-hydroxy-1-methyl-3-(4-nitrophenyl)urea,
1-hydroxy-1-methyl-3-(4-phenoxyphenyl)urea,
1-hydroxy-1-(1-methylethyl)-3-[3-(methylthio)phenyl]urea,
1-hydroxy-1-(1-methylethyl)-3-phenylurea,
3-(4-fluorophenyl)-1-hydroxy-1-(1-methylethyl)urea,
3-(4-bromophenyl)-1-hydroxy-1-(1-methylethyl)urea,
3-(2-fluorophenyl)-1-hydroxy-1-(1-methylethyl)urea,
1-hydroxy-1-(1-methylethyl)-3-(3-methylphenyl)urea,
1-hydroxy-3-(3-methoxyphenyl)-1-(1-methylethyl)urea,
1-hydroxy-3-(4-methoxyphenyl)-1-(1-methylethyl)urea,
3-(2-chlorophenyl)-1-hydroxy-1-(1-methylethyl)urea,
1-hydroxy-1-(1-methylethyl)-3-(2-methylphenyl)urea,
3-(2,6-dimethylphenyl)-1-hydroxy-1-(1-methylethyl)urea,
3-(4-butylphenyl)-1-hydroxy-1-(1-methylethyl)urea,
3-(2,5-dimethoxyphenyl)-1-hydroxy-1-(1-methylethyl)urea,
1-hydroxy-3-(2-methoxyphenyl)-1-(1-methylethyl)urea,
1-hydroxy-1-(1-methylethyl)-3-(4-nitrophenyl)urea,
1-cyclohexyl-1-hydroxy-3-[4-(methylthio)phenyl]urea,
1-cyclohexyl-1-hydroxy-3-[3-(methylthio)phenyl]urea,
1-hydroxy-3-(3-methoxyphenyl)urea,
1-hydroxy-3-[3-(methylthio)phenyl]urea,
1-cyclooctyl-1-hydroxy-3-phenylurea,
1-cyclooctyl-1-hydroxy-3-(4-methoxyphenyl)urea,
1-cyclooctyl-1-hydroxy-3-(4-nitrophenyl)urea,
1-(1-ethylpropyl)-1-hydroxy-3-[4-(methylthio)phenyl]urea,
1-(1-ethylpropyl)-1-hydroxy-3-(4-nitrophenyl)urea,
3-(4-bromophenyl)-1-(1-ethylpropyl)-1-hydroxyurea,
1-ethyl-1-hydroxy-3-phenylurea,
1-hydroxy-1-(3-methylbutyl)-3-phenylurea,
1-(2-ethoxyethyl)-1-hydroxy-3-phenylurea,
1-cyclopentyl-1-hydroxy-3-phenylurea,
1-(2-ethylhexyl)-1-hydroxy-3-phenylurea,
1-(3,3-dimethylbutyl)-1-hydroxy-3-phenylurea,
1-hydroxy-3-phenyl-1-(3,5,5-trimethylhexyl)urea,
6-(1-hydroxy-3-phenylureido)-1-hexanoic acid ethyl ester,
1-cycloheptyl-1-hydroxy-3-phenylurea,
1-hydroxy-1-octyl-3-phenylurea,
1-dodecyl-1-hydroxy-3-phenylurea,
1-hydroxy-1-(2-methylpropyl)-3-phenylurea,
1-hydroxy-3-phenyl-1-propylurea,
1-hydroxy-1-pentyl-3-phenylurea,
3-(4-butylphenyl)-1-hydroxy-1-pentylurea,
1-hydroxy-1-(2-methylpropyl)-3-[3-(methylthio)phenyl]urea,
1-hydroxy-1-methyl-3-[3-(methylsulfonyl)phenyl]urea,
1-hydroxy-1-(1-methylethyl)-3-[3-(methylsulfonyl)phenyl]urea,
1-hydroxy-1-(1-methylethyl)-3-[3-(methylsulfinyl)phenyl]urea,
1-hydroxy-1-(1-methylethyl)-3-[4-(methylsulfonyl)phenyl]urea,
1-hydroxy-1-(1-methylethyl)-3-[4-(methylsulfinyl)phenyl]urea,
1-hydroxy-1-methyl-3-[4-(methylsulfinyl)phenyl]urea,
1-hydroxy-1-methyl-3-[4-(methylsulfonyl)phenyl]urea,
1-hydroxy-1-(1-methylethyl)-3-(3,4,5-trimethoxyphenyl)urea,
1-hydroxy-1-(1-methylethyl)-3-(2,4,5-trimethylphenyl)urea,
1-hydroxy-1-(1-methylbutyl)-3-phenylurea,
1-hydroxy-1-(1-methylpropyl)-3-phenylurea,
1-hydroxy-1-(1-propylbutyl)-3-phenylurea,
1-hydroxy-1-(1-ethylbutyl)-3-phenylurea,
1-hydroxy-1-(1-ethylpropyl)-3-(4-phenoxyphenyl)urea,
1-hydroxy-1-(1-ethylpropyl)-3-(3,5-bis(trifluoromethyl)phenyl)urea,
1-hydroxy-1-(1-ethylpropyl)-3-methyl-3-phenylurea,
1-hydroxy-1,3-dimethyl-3-phenylurea,
1-hydroxy-1-(1-ethylpropyl)-3-(2-phenoxyphenyl)urea,
1-hydroxy-1-(1-ethylpropyl)-3-(3-phenoxyphenyl)urea,
1-hydroxy-1-(1-ethylpropyl)-3-(4-benzylphenyl)urea,
1-hydroxy-1-(1-ethylpropyl)-3-(4-benzoylphenyl)urea,
1-hydroxy-1-(1-ethylpropyl)-3-(4-benzyloxyphenyl)urea,
1-hydroxy-1-(1-ethylpropyl)-3-[4-(cyclohexylmethoxy)phenyl]urea,
1-hydroxy-1-(1-ethylpropyl)-3-[4-(3-phenylpropyloxy)phenyl]urea,
1-hydroxy-1-(1-ethylpropyl)-3-(biphenyl-4-yl)urea,
1-hydroxy-1-(1-ethylpropyl)-3-(3-cyclopentyloxy-4-methoxyphenyl)urea, and
1-hydroxy-1-(1-ethylpropyl)-3-(4'-octyloxybiphenyl-4-yl)urea.

1-Hydroxy-1-methyl-3-[4-(methylthio)phenyl]urea, 1-hydroxy-1-(1-methylethyl)-3-[4-(methylthio)phenyl]urea, 1-(1-ethylpropyl)-1-hydroxy-3-(4-methylthio)phenyurea, 1-(1-ethylpropyl)-1-hydroxy-3-phenylurea, 1-hydroxy-1-methyl-3-(4-phenoxyphenyl)urea, 1-hydroxy-1-(1-ethylpropyl)-3-(4-phenoxyphenyl)urea, 1-hydroxy-1-(1-ethylpropyl)-3-(2-phenoxyphenyl)urea, 1-hydroxy-1-(1-methylethyl)-3-(4-butylphenyl)urea, 1-hydroxy-1-(1-methylpropyl)-3-phenylurea, and 1-hydroxy-1-(1-ethylpropyl)-3-(3-phenoxyphenyl)urea are most preferred.

Compounds useful in the practice of the method of this invention can be prepared in accordance with the Reaction Schemes described below or through modifications thereof that will be readily apparent to those skilled in the art. A suitable route can be selected with due consideration of the particular R, R', or R" substituent, commercial availability of some starting materials, and the like.

Certain compounds useful in the practice of the method of this invention can be prepared according to Reaction Scheme I, wherein n, R and R' are as defined above.

Reaction Scheme I

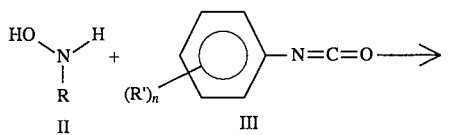

Reaction Scheme I involves reacting a hydroxylamine of Formula II with an aryl isocyanate of Formula III to afford a hydroxyurea of Formula IV. (Formula IV is a subgenus of Formula I.) Many hydroxylamines of Formula II are commercially available. Others may be readily prepared using conventional methods, for example, conversion of a suitable ketone to its oxime followed by reduction to the requisite hydroxylamine. Many isocyanates of Formula III are also commercially available. Others may be readily prepared using conventional methods, for example, Curtius rearrangement, Hofmann rearrangement, Schmidt reaction, or reacting an aniline with phosgene. The reaction in Reaction Scheme I can be conducted at ambient temperature by dropwise addition of the isocyanate to a solution of the hydroxylamine in a suitable solvent (e.g., an aprotic solvent such as diethyl ether or tetrahydrofuran). When a salt (e.g., a hydrochloride) of the hydroxylamine is used, it is converted to the free base using conventional means (e.g., reacting with one equivalent of base in a suitable solvent) prior to its reaction with the isocyanate.

Certain compounds of Formula I can also be prepared according to Reaction Scheme II, wherein n, R and R' are as defined above. Reaction Scheme II, however, is generally not suitable for compounds in which R' is a strongly electron withdrawing group (e.g., nitro).

Reaction Scheme II

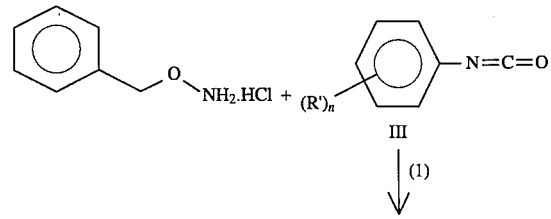

-continued
Reaction Scheme II

In step (1) of Reaction Scheme II, O-benzylhydroxylamine hydrochloride is reacted, according to the method of Reaction Scheme I, with an isocyanate of Formula III to afford a 1-benzyloxy-3-phenylurea of Formula V. In step (2) the compound of Formula V is alkylated under conventional conditions, e.g., by reacting with a compound of formula RBr in the presence of a base such as sodium hydride and in a suitable polar aprotic solvent (e.g., N,N-dimethylformamide) to afford a benzyloxy urea of Formula VI. The reaction can be heated if necessary or desirable. In step (3) of Reaction Scheme II, the benzyloxy urea of Formula VI is debenzylated using conventional means (e.g., hydrogenolysis) to afford the hydroxy urea of Formula IV.

Certain compounds of Formula I can also be prepared according to Reaction Scheme III, wherein n, R and R' are as defined above.

Reaction Scheme III

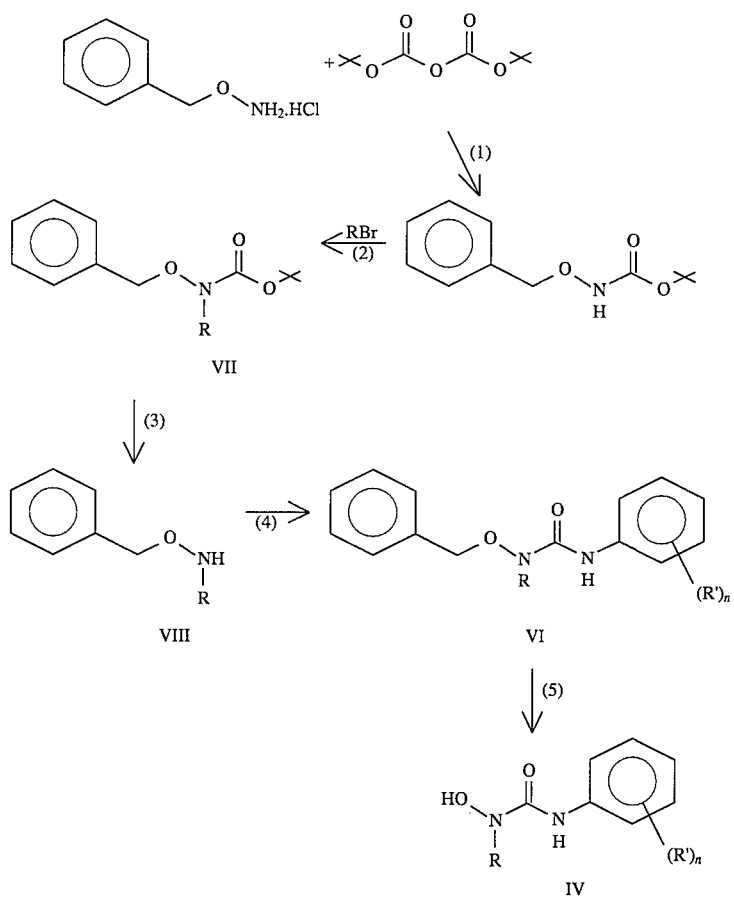

In step (1) of Reaction Scheme III, O-benzylhydroxylamine hydrochloride is reacted with di-tert-butyldicarbonate to provide tert-butyl N-benzyloxycarbamate. In step (2) tert-butyl benzyloxycarbamate is alkylated under conventional conditions, e.g., by reacting with a compound of formula RBr in the presence of a base such as sodium hydride and in a suitable polar aprotic solvent (e.g., N,N-dimethylformamide). The alkylation affords a carbamate of Formula VII. The reaction can be heated if necessary or desirable.

In step (3) of Reaction Scheme III, the carbamate of Formula VII is deblocked by treating with trifluoroacetic acid in a suitable solvent (e.g., methylene chloride) to afford an O-benzylhydroxylamine of Formula VIII. In step (4) the O-benzylhydroxylamine of Formula VIII is reacted according to the method of Reaction Scheme I with an isocyanate of Formula III to afford a benzyloxy urea of Formula VI. In step (5) the benzyloxy urea is debenzylated using conventional means (e.g., hydrogenolysis) to afford a hydroxy urea of Formula IV.

Certain compounds of Formula I can also be prepared according to Reaction Scheme IV, wherein n, R, R' and R" are as defined above (provided, however, that R" is not H).

In step (1) of Reaction Scheme IV, an O-benzylhydroxylamine of Formula VIII is reacted with a carbamoyl chloride of Formula IX to afford a benzyloxy urea of Formula X. O-benzylhydroxylamines of Formula VIII may be prepared according to the method of Reaction Scheme III. Many carbamoyl chlorides of Formula IX are commercially available. Others may be readily prepared using conventional methods, for example, reacting an N-alkylaniline with phosgene. The reaction in step (1) can be carried out in a sealed tube at an elevated temperature in the presence of a base (e.g., triethylamine) in a suitable solvent (e.g., an aprotic solvent such as tetrahydrofuran). In step (2) of Reaction Scheme IV, the benzyloxy urea of Formula X is debenzylated using conventional means (e.g., hydrogenolysis) to afford the hydroxyurea of Formula XI.

Reaction Scheme IV

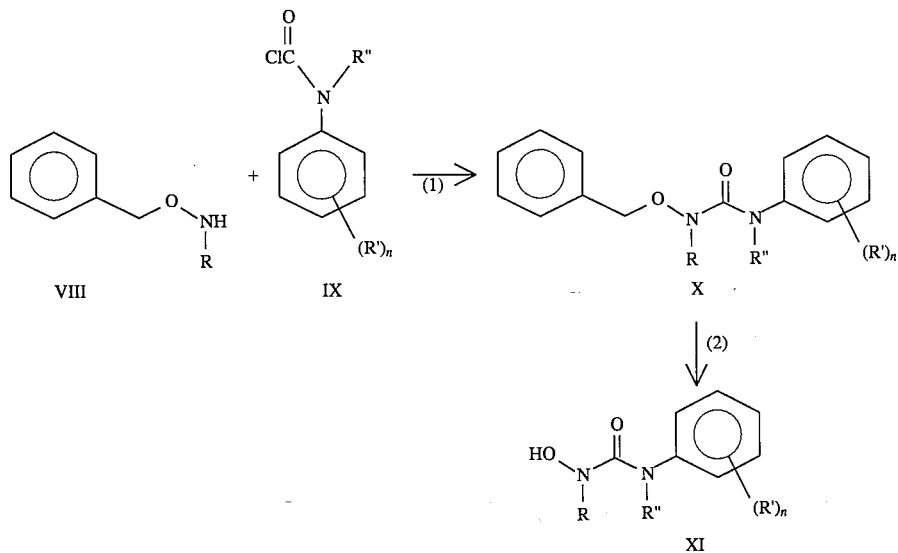

Certain compounds of Formula I can also be prepared according to Reaction Scheme V, wherein n, R, R' and R" are as defined above, provided however that R" is not hydrogen.

In step (1) of Reaction Scheme V, O-benzylhydroxylamine hydrochloride is reacted with a carbamoyl chloride of Formula IX to afford a benzyloxy urea of Formula XII. The reaction can be conducted at ambient temperature by combining the reactants in a suitable solvent (e.g., diethyl ether). The O-benzylhydroxylamine hydrochloride is converted to the free base using conventional means (e.g., reacting with one equivalent of base in a suitable solvent) prior to its reaction with the carbamoyl chloride. In step (2) of Reaction Scheme V, the compound of Formula XII is alkylated under conventional conditions, e.g., by reacting with an alkyl halide in the presence of a base such as sodium hydride and in a suitable polar aprotic solvent (e.g., N,N-dimethylformamide) to afford a benzyloxy urea of Formula X. In step (3) of Reaction Scheme V, the benzyloxy urea of Formula X is debenzylated using conventional means (e.g., hydrogenolysis) to afford the hydroxyurea of Formula XI.

Reaction Scheme V

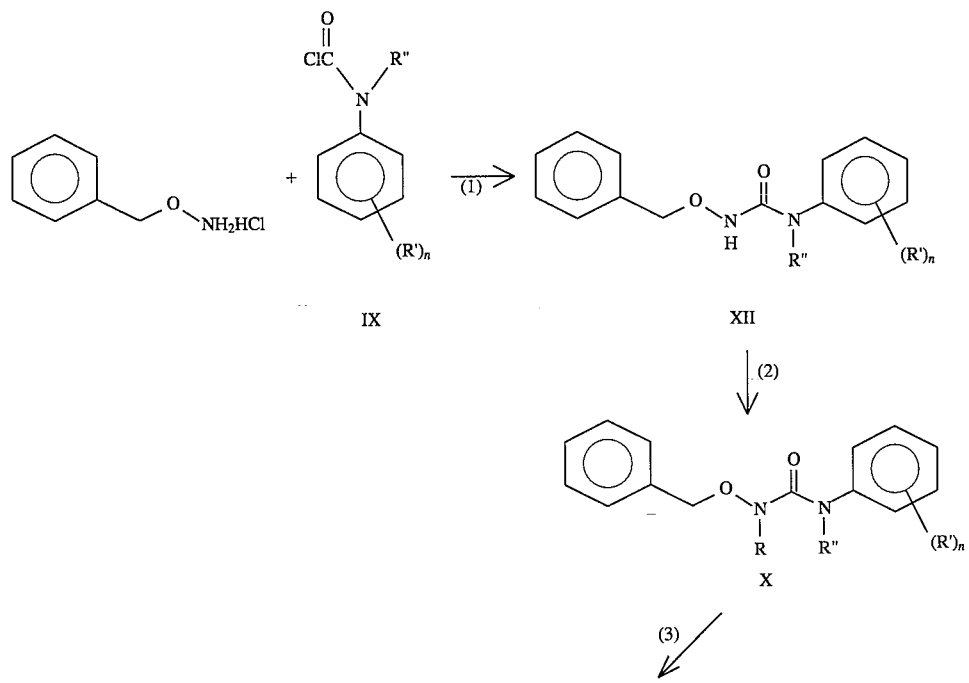

-continued
Reaction Scheme V

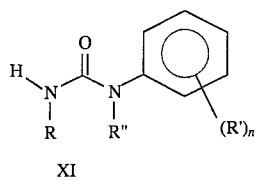

XI

Certain compounds of Formula I can be prepared by elaboration of the R' group by conventional means (e.g., oxidation of an alkylthio group to an alkylsulfonyl group) at an appropriate stage of synthesis.

The compounds of Formula I wherein M is a pharmaceutically acceptable cation can be prepared by combining in a polar solvent a compound of Formula I where M is hydrogen with an equimolar amount of a relatively strong base, e.g., a base of the formula $M(OH)_x$ wherein M is the pharmaceutically acceptable cation and x is the valence of such cation. Isolation of the salt can be facilitated by the addition of a solvent, such as diethyl ether, in which the salt is insoluble.

A compound of Formula I can be formulated for various routes of administration (e.g., oral administration by tablet, capsule, oral suspension, or the like) in an appropriate pharmaceutically acceptable vehicle and adjuvants and excipients suitable for the selected dosage form. Methods of manufacture of such pharmaceutical compositions are well known to those skilled in the art and disclosed, e.g., in *Remington's Pharmaceutical Sciences*, 18th Edition, 1990 Mack Publishing Company, A. R. Gennaro, Editor. Consequently, particular formulations suitable for a selected route of administration can be readily identified and prepared by those skilled in the art. A solid dosage form, for example, contains a compound of Formula I, and one or more ingredients selected from the group consisting of diluents (e.g., dicalcium phosphate, calcium sulfate, lactose, mannitol, cellulose, kaolin, sodium chloride, starch, sucrose, inositol, sorbitol), binders (e.g., starch, gelatin, sucrose, glucose, dextrose, molasses, lactose, natural and synthetic gums), lubricants (e.g., talc, magnesium stearate, calcium stearate, stearic acid, hydrogenated vegetable oils, polyethylene glycols), disintegrants (e.g., corn starch, potato starch, clays, cellulose, alginates), coloring agents, and flavoring agents.

The compound of Formula I is administered in an amount effective to inhibit leukotriene biosynthesis. The amount that constitutes an amount effective to inhibit leukotriene biosynthesis will depend on the particular compound, the particular formulation, the route of administration, and the intended therapeutic effect. Those skilled in the art can determine such an amount with due consideration of such factors.

A number of the compounds of Formula I are shown by the Examples below to inhibit leukotriene biosynthesis. These results suggest utility in treating conditions mediated by leukotrienes, such as arthritis, rheumatoid arthritis, osteoarthritis, allergic rhinitis, adult respiratory distress syndrome, inflammatory bowel disease, ischemic induced myocardial injury, reperfusion injury, gout, asthma, stroke, psoriasis, spinal cord injury, and traumatic brain injury.

In the following syntheses, the structures of the final compounds (i.e. compounds of Formula I) and of intermediates were confirmed by nuclear magnetic resonance spectroscopy.

Compound 1

1-Hydroxy-1-methyl-3-[4-(methylthio)phenyl]urea

N-Methylhydroxylamine hydrochloride (1.1 g, 13 mmol) was dissolved in water (2 mL) then combined with diethyl ether (15 mL). The mixture was cooled in an ice bath then combined with a solution of sodium hydroxide (0.53 g, 13 mmol) in water (2 mL). The reaction mixture was allowed to stir for several minutes then 4-(methylthio)phenyl isocyanate (2.1 g, 13 mmol) was added dropwise via Pasteur pipette. A heavy white precipitate formed almost immediately. Diethyl ether (20 mL) was added and the reaction mixture was allowed to stir at ambient temperature overnight. The solid was isolated by filtration then recrystallized from 1,2-dichloroethane to afford 1.65 g of the desired product as a white crystalline solid, m.p. 146°–148° C. Analysis: Calculated for $C_9H_{12}N_2O_2S$: %C, 50.93; %H, 5.70; %N, 13.20; Found: %C, 50.82; %H, 5.63; %N, 13.11.

Compounds 2–14

Using the general method of Compound 1, N-methylhydroxylamine hydrochloride was reacted with an isocyanate of Formula III to provide the compounds of Formula I shown in Table 1. The melting points and elemental analyses are shown in Table 2.

TABLE 1

| Compound Number | Compound of Formula I<br>M = H; R = $CH_3$; R" = H; R' = |
|---|---|
| 2 | 3-trifluoromethylsulfonoxy |
| 3 | 3-methylthio |
| 4 | 3-trifluoromethylthio |
| 5 | 3-methoxy |
| 6 | 3-bromo |
| 7 | 3-methyl |
| 8 | 3-fluoro |
| 9 | 3-nitro |
| 10 | hydrogen |
| 11 | 4-fluoro |
| 12 | 4-butyl |
| 13 | 4-nitro |
| 14 | 4-phenoxy |

TABLE 2

| Compound Number | m.p. (°C.) | Formula | Calculated % C | % H | % N | Found % C | % H | % N |
|---|---|---|---|---|---|---|---|---|
| 2 | 132–133 | $C_9H_9F_3N_2O_5S$ | 34.4 | 2.9 | 8.9 | 34.5 | 2.9 | 9.1 |
| 3 | 127–131 | $C_9H_{12}N_2O_2S$ | 50.93 | 5.7 | 13.2 | 51.06 | 5.76 | 13.29 |
| 4 | 129–130.5 | $C_9H_9F_3N_2O_2S$ | 40.6 | 3.4 | | 40.7 | 3.5 | |
| 5 | 115–117 | $C_9H_{12}N_2O_3$ | 55.1 | 6.16 | 14.28 | 55.17 | 6.21 | 14.13 |
| 6 | 135–136 | $C_8H_9BrN_2O_2$ | 39.21 | 3.7 | 11.43 | 39.3 | 3.52 | 11.19 |
| 7 | 107–109 | $C_9H_{12}N_2O_2$ | 59.99 | 6.71 | 15.54 | 59.76 | 6.58 | 15.38 |
| 8 | 110–112 | $C_8H_9FN_2O_2$ | 52.17 | 4.93 | 15.21 | 51.99 | 4.86 | 15.05 |
| 9 | 124–126 | $C_8H_9N_3O_4$ | 45.5 | 4.3 | 19.9 | 45.31 | 4.16 | 19.87 |
| 10 | 98–100 | $C_8H_{10}N_2O_2$ | 57.82 | 6.07 | 16.86 | 57.65 | 6.07 | 16.78 |
| 11 | 123–125 | $C_8H_9FN_2O_2$ | 52.17 | 4.93 | 15.21 | 51.78 | 4.84 | 14.99 |
| 12 | 94.9–95.3 | $C_{12}H_{18}N_2O_2$ | 64.84 | 8.16 | 12.6 | 65.15 | 8.08 | 12.58 |
| 13 | 179–180 | $C_8H_9N_3O_4$ | 45.5 | 4.3 | 19.9 | 45.97 | 4.05 | 19.89 |
| 14 | 130–131 | $C_{14}H_{14}N_2O_3$ | 65.11 | 5.46 | 10.85 | 64.91 | 5.35 | 10.72 |

Compound 15

1-Hydroxy-1-(1-methylethyl)-3-[4-(methylthio)phenyl]urea

N-Isopropylhydroxylamine hydrochloride (1.35 g, 12.1 mmol) was dissolved in water (2 mL) then combined with diethyl ether (25 mL) followed by the addition of a solution of sodium hydroxide (0.48 g, 12.1 mmol) in water (2 mL). The reaction mixture was allowed to stir for several minutes then 4-(methylthio)phenyl isocyanate (2.0 g, 12.1 mmol) was added via pipette. A white precipitate formed. The reaction mixture was allowed to stir at ambient temperature overnight. The solid was isolated by filtration then dissolved in hot ethyl acetate. The ethyl acetate solution was dried over magnesium sulfate then concentrated under vacuum. The precipitate was collected and dried to afford 1.60 g of the desired product as a crystalline solid, m.p. 150.0°–150.3° C. Analysis: Calculated for $C_{11}H_{16}N_2O_2S$: %C, 54.98; %H, 6.71; %N, 11.66; Found: %C, 54.96; %H, 6.53; %N, 11.61.

Compounds 16–30

Using the general method of Compound 15, N-isopropylhydroxylamine hydrochloride was reacted with an isocyanate of Formula III to provide the compounds of Formula I shown in Table 3. The melting points and elemental analyses are shown in Table 4.

TABLE 3

| Compound Number | Compound of Formula I<br>M = H; R = 1-methylethyl; R" = H; R' = |
|---|---|
| 16 | 3-methylthio |
| 17 | hydrogen |
| 18 | 4-fluoro |
| 19 | 4-bromo |
| 20 | 2-fluoro |
| 21 | 3-methyl |
| 22 | 3-methoxy |
| 23 | 4-methoxy |
| 24 | 2-chloro |
| 25 | 2-methyl |
| 26 | 2,6-dimethyl |
| 27 | 4-butyl |
| 28 | 2,5-dimethoxy |
| 29 | 2-methoxy |
| 30 | 4-nitro |

TABLE 4

| Compound Number | m.p. (°C.) | Formula | Calculated % C | % H | % N | Found % C | % H | % N |
|---|---|---|---|---|---|---|---|---|
| 16 | 125–127 | $C_{11}H_{16}N_2O_2S$ | 54.98 | 6.71 | 11.66 | 55.13 | 6.68 | 11.64 |
| 17 | 124–126 | $C_{10}H_{14}N_2O_2$ | 61.84 | 7.27 | 14.42 | 61.56 | 7.2 | 14.09 |
| 18 | 134.5–134.9 | $C_{10}H_{13}FN_2O_2$ | 56.6 | 6.17 | 13.2 | 56.88 | 6.13 | 13.21 |
| 19 | 141.2–141.6 | $C_{10}H_{13}BrN_2O_2$ | 43.98 | 4.8 | 10.26 | 43.93 | 4.72 | 10.16 |
| 20 | 109.3–111.1 | $C_{10}H_{13}FN_2O_2$ | 56.6 | 6.17 | 13.2 | 56.34 | 6.06 | 13.07 |
| 21 | 105.0–106.1 | $C_{11}H_{16}N_2O_2$ | 63.44 | 7.74 | 13.45 | 63.34 | 7.76 | 13.44 |
| 22 | 121.8–124.3 | $C_{11}H_{16}N_2O_3$ | 58.91 | 7.19 | 12.49 | 58.58 | 7.03 | 12.33 |
| 23 | 141.1–141.5 | $C_{11}H_{16}N_2O_3$ | 58.91 | 7.19 | 12.49 | 58.86 | 7.24 | 12.45 |
| 24 | 116.5–119.5 | $C_{10}H_{13}ClN_2O_2$ | 52.52 | 5.73 | 12.25 | 52.69 | 5.73 | 12.21 |
| 25 | 119.8 | $C_{11}H_{16}N_2O_2$ | 63.44 | 7.74 | 13.45 | 63.05 | 7.76 | 13.42 |
| 26 | 154.1–155.3 | $C_{12}H_{18}N_2O_2$ | 64.84 | 8.16 | 12.6 | 64.93 | 8.15 | 12.55 |
| 27 | 118.1–118.6 | $C_{14}H_{22}N_2O_2$ | 67.17 | 8.86 | 11.19 | 67.2 | 8.71 | 11.13 |
| 28 | 153.1–153.3 | $C_{12}H_{18}N_2O_4$ | 56.68 | 7.13 | 11.02 | 56.64 | 7.23 | 10.94 |
| 29 | 134.5–134.7 | $C_{11}H_{16}N_2O_3$ | 58.91 | 7.19 | 12.49 | 58.85 | 7.2 | 12.3 |
| 30 | 148.2–149.7 | $C_{10}H_{13}N_3O_4$ | 50.21 | 5.48 | 17.56 | 50.16 | 5.29 | 17.37 |

Compound 31

1-Cyclohexyl-1-hydroxy-3-[4-(methylthio)phenyl]urea

Using the general method of Compound 1, N-cyclohexylhydroxylamine hydrochloride (1.5 g, 10 mmol) was reacted with 4-(methylthio)phenyl isocyanate (1.6 g, 10 mmol) to provide 0.60 g of the desired product as a white solid m.p. 151°–153° C. Analysis: Calculated for $C_{14}H_{20}N_2O_2S$: %C, 59.97; %H, 7.19; %N, 9.99; Found: %C, 60.06; %H, 7.14; %N, 9.95.

Compound 32

1-Cyclohexyl-1-hydroxy-3-[3-(methylthio)phenyl]urea

Using the general method used to prepare Compound 1, N-(cyclohexyl)hydroxylamine hydrochloride (1.5 g, 10 mmol) was reacted with 3-(methylthio)phenyl isocyanate (1.6 g, 10 mmol) to provide 0.76 g of the desired product as a white solid m.p. 147.2°–147.7° C. Analysis: Calculated for $C_{14}H_{20}N_2O_2S$: %C, 59.97; %H, 7.19; %N, 9.99; Found: %C, 60.16; %H, 6.95; %N, 9.96.

Compounds 33–34

Using the general method of Compound 1, hydroxylamine hydrochloride was reacted with an isocyanate of Formula III to provide the compounds of Formula I shown in Table 5. The melting points and elemental analyses are shown in Table 6.

TABLE 5

| Compound Number | Compound of Formula I M = H; R = H; n = 1; R" = H; R' = |
|---|---|
| 33 | 3-methoxy |
| 34 | 3-methylthio |

TABLE 6

| Compound Number | m.p. (°C.) | Formula | Elemental Analyses | | | | | |
|---|---|---|---|---|---|---|---|---|
| | | | Calculated | | | Found | | |
| | | | % C | % H | % N | % C | % H | % N |
| 33 | 140–142 | $C_8H_{10}N_2O_3$ | 52.74 | 5.53 | 15.38 | 52.57 | 5.41 | 15.21 |
| 34 | 147–149 | $C_8H_{10}N_2O_2S$ | 48.47 | 5.08 | 14.13 | 48.66 | 5.04 | 13.85 |

Compound 36

1-Cyclooctyl-1-hydroxy-3-phenylurea

Part A

A solution containing cyclooctanone (12.6 g, 0.1 mol) and hydroxylamine hydrochloride (14.0 g, 0.2 mole) in a mixture of pyridine (40 mL, 0.5 mole) and ethanol (50 mL) was stirred at ambient temperature for about 15 hours. The solvent was then removed by rotary evaporation. The residue was dissolved in diethyl ether (300 mL) then washed with hydrochloric acid (2×100 mL). The aqueous layer was extracted with diethyl ether (2×150 mL). The ether extracts were combined, dried over magnesium sulfate then concentrated to provide cyclooctanone oxime as a white solid.

Part B

A solution containing cyclooctanone oxime (9.0 g, 64 mmol) in glacial acetic acid (90 mL) was slowly charged with sodium cyanoborohydride (6.0 g, 95 mmol). The reaction mixture was stirred at ambient temperature for 18 hours then adjusted to pH=9 by the slow addition of cold 2N sodium hydroxide. The resulting precipitate was collected and dried to provide cyclooctyl hydroxylamine as a white solid.

Part C

A solution containing cyclooctyl hydroxylamine (3.0 g, 21 mmol) in tetrahydrofuran (75 mL) was slowly charged with phenyl isocyanate (2.3 mL, 21 mmol). The reaction mixture was allowed to stir at ambient temperature for 40 hours. The solvent was evaporated to provide 5.5 g of crude product which was recrystallized from hexanes:ethyl acetate (4:1) to provide 3.1 g of the desired product as white needles, m.p. 138°–139° C. Analysis: Calculated for $C_{15}H_{22}N_2O_2$: %C, 68.67; %H, 8.45; %N, 10.68; Found: %C, 68.36; %H, 8.28; %N, 10.64.

Compound 37

1-Cyclooctyl-1-hydroxy-3-(4-methoxyphenyl)urea

A solution containing cyclooctyl hydroxylamine (Compound 36 Part B, 2.0 g, 14 mmol) in tetrahydrofuran (50 mL) was slowly charged with 4-methoxyphenyl isocyanate (2.0 mL, 15 mmol). The reaction mixture was allowed to stir at ambient temperature for 20 hours. A white precipitate was isolated by filtration then washed with cold hexane. A second crop was isolated from the filtrate. The solids were combined and dried to provide 3.2 g of the desired product as a white solid, m.p. 166°–167° C. Analysis: Calculated for $C_{16}H_{24}N_2O_3$: %C, 65.73; %H, 8.27; %N, 9.58; Found: %C, 65.31; %H, 7.98; %N, 9.47.

Compound 38

1-Cyclooctyl-1-hydroxy-3-(4-nitrophenyl)urea

Using the general method of Compound 36 Part C, cyclooctyl hydroxylamine (Compound 36 Part B, 1.0 g, 7.0 mmol) was reacted with 4-nitrophenyl isocyanate (1.2 g, 7.3 mmol) to provide 1.1 g of the desired product as a pale yellow solid, m.p. 143°–144° C. Analysis: Calculated for $C_{15}H_{21}N_3O_4$: %C, 58.62; %H, 6.89: %N, 13.67; Found: %C, 58.5; %H, 7.56; %N, 13.32.

Compound 39

1-(1-Ethylpropyl)-1-hydroxy-3-[4-(methylthio) phenyl]urea

Part A

A solution of sodium hydroxide (40 g, 1 mole) in water (650 mL) was cooled to 25° C. then added over a period of 3 minutes to a solution of 3-pentanone (43 g, 0.5 mole) and hydroxylamine hydrochloride (69 g, 1 mole) in ethanol (250 mL). The temperature rose to 37° C. and after several minutes a layer of brown oil separated out. The reaction mixture was heated on a steam bath with occasional swirling until a clear, colorless solution was obtained. The mixture was heated for an additional hour, the ethanol was removed under reduced pressure and the reaction mixture was extracted with ethyl acetate (2×250 mL). The extracts were combined, dried over magnesium sulfate and concentrated. The residue was distilled to provide 7.5 g of 3-pentanone oxime, b.p. 165°–8° C.

Part B

A solution of 3-pentanone oxime (10.0 g, 0.1 mole) in glacial acetic acid (125 mL) was slowly charged with sodium cyanoborohydride (9.4 g, 0.15 mole) over a period of 1 hour. The reaction mixture was maintained at ambient temperature for 18 hours, chilled in an ice bath, adjusted to pH=9 by the slow addition of 4N sodium hydroxide and then extracted with ethyl acetate (6×150 mL). The extracts were combined, dried over sodium sulfate then concentrated to provide 10.1 g of N-(1-ethylpropyl)hydroxylamine as a pale yellow oil.

Part C 4-(Methylthio)phenyl isocyanate (5.6 g, 34 mmol) was added dropwise over a period of 10 minutes to a solution of N-(1-ethylpropyl)hydroxylamine (3.5 g, 34 mmol) in diethyl ether (about 50 mL). The reaction mixture was stirred at ambient temperature for 1 hour. The precipitate was isolated by filtration and dried to provide 2.9 g of the desired product as a solid, m.p. 140.4°–141.0° C. Analysis: Calculated for $C_{13}H_{20}N_2O_2S$: %C, 58.18; %H, 7.51; %N, 10.44; Found: %C, 58.12; %H, 7.27; %N, 10.4.

Compound 40

1-(1-Ethylpropyl)-1-hydroxy-3-(4-nitrophenyl)urea

Using the method of Compound 39 Part C, N-(1-ethylpropyl)hydroxylamine (Compound 39 Part B, 1.15 g, 11.3 mmol) was reacted with 4-nitrophenyl isocyanate (1.85 g, 11.3 mmol) to provide 1.95 g of the desired product as a solid, m.p. 169°–170° C. Analysis: Calculated for $C_{12}H_{17}N_3O_4$: %C, 53.92; %H, 6.41; %N, 15.72; Found: %C, 53.85; %H, 6.36; %N, 15.55.

Compound 41

3-(4-Bromophenyl)-1-(1-ethylpropyl)-1-hydroxyurea

Using the method of Compound 39 Part C, N-(1-ethylpropyl)hydroxylamine (2.6 g, 25 mmol) was reacted with 4-bromophenyl isocyanate (5 g, 25 mmol) to provide 2.1 g of the desired product as a solid, m.p. 129°–131° C. Analysis: Calculated for $C_{12}H_{17}BrN_2O_2$: %C, 47.86; %H, 5.69; %N, 9.3; Found: %C, 47.79; %H, 5.54; %N, 9.25.

Compound 42

1-(1-Ethylpropyl)-1-hydroxy-3-phenylurea

Part A

Under a nitrogen atmosphere, a flask was charged sequentially with O-benzylhydroxylamine hydrochloride (37.5 g, 0.23 mole), water (40 mL) and diethyl ether (400 mL). The resulting mixture was cooled to 0° C. and a solution of sodium hydroxide (9.4 g, 0.23 mole) in water (40 mL) was added dropwise. After 0.5 hour, phenyl isocyanate (25.5 mL, 0.23 mole) was added. A white precipitate formed. The reaction was maintained at ambient temperature for 2 hours. The precipitate was isolated by filtration, washed with water and dried to provide 46.2 g of 1-benzyloxy-3-phenyl urea as a white crystalline solid.

Part B

Under a nitrogen atmosphere, a flask was charged with sodium hydride (1.15 g 60% NaH in mineral oil, 29 mmol). Residual oil was washed from the sodium hydride using several portions of hexanes. N,N-Dimethylformamide (50 mL) was added followed by the dropwise addition of a solution of 1-benzyloxy-3-phenylurea (7.0 g, 29 mmol) in N,N-dimethylformamide (20 mL). Hydrogen evolution occurred immediately. The reaction was stirred for 0.5 hr then 3-bromopentane (4.0 mL, 32 mmol) was added dropwise. The reaction mixture was heated at 60° C. for 15 hours then allowed to cool to room temperature. The reaction was quenched with water then extracted with several portions of diethyl ether. The ether extracts were combined, washed with water and brine, dried over magnesium sulfate and then concentrated to provide 8.7 g of crude product as a pale yellow solid. The crude product was purified by flash chromatography (silica gel; 9:1 hexanes:ethyl acetate)to provide 5.7 g of 1-benzyloxy-1-(1-ethylpropyl)-3-phenylurea as a white solid, m.p. 45.0°–45.6° C.

Part C

A solution of 1-benzyloxy-1-(1-ethylpropyl)-3-phenylurea (4.9 g, 15.7 mmol) in ethanol (90 mL) was charged sequentially with ammonium formate (3.5 g, 55.5 mmol) and 10% palladium on carbon (1.7 g). The resulting black suspension was stirred at ambient temperature for 2 hours. The reaction mixture was vacuum filtered through a pad of Celite™ filter agent. A precipitate formed in the filtrate and was isolated to provide 3.6 g of crude product as a white powder. This material was recrystallized from hexanesethyl acetate to provide 2.7 g of the desired product as very fine needles, m.p. 129.5°–129.8° C. Analysis: Calculated for $C_{12}H_{18}N_2O_2$: %C, 64.84; %H, 8.16; %N, 12.6; Found: %C, 64.79; %H, 8.41; %N, 12.38.

Compounds 43–53

Using the general method of Compound 42 Part B, 1-benzyloxy-3-phenylurea was reacted with compounds of formula RBr to provide intermediates of Formula VI with n=0. Using the general method of Compound 42 Part C, the intermediates of Formula VI were debenzylated to provide the compounds of Formula I shown in Table 7. The melting points and elemental analyses are shown in Table 8.

TABLE 7

| Compound Number | Compound of Formula I<br>M = H; n = 0; R" = H; R = |
| --- | --- |
| 43 | ethyl |
| 44 | 3-methylbutyl |
| 45 | 2-ethoxyethyl |
| 46 | cyclopentyl |
| 47 | 2-ethylhexyl |
| 48 | 3,3-dimethylbutyl |
| 49 | 3,5,5-trimethylhexyl |
| 50 | 5-carbethoxypentyl |
| 51 | cycloheptyl |
| 52 | octyl |
| 53 | dodecyl |

TABLE 8

| Compound Number | m.p. (°C.) | Formula | Elemental Analyses Calculated %C | %H | %N | Found %C | %H | %N |
| --- | --- | --- | --- | --- | --- | --- | --- | --- |
| 43 | 95.6–96.0 | $C_9H_{12}N_2O_2$ | 59.99 | 6.71 | 15.54 | 59.85 | 6.63 | 15.68 |
| 44 | 106.2–106.5 | $C_{12}H_{18}N_2O_2$ | 64.84 | 8.16 | 12.6 | 64.82 | 8.25 | 12.6 |
| 45 | 54.9–55.4 | $C_{11}H_{16}N_2O_3$ | 58.91 | 7.19 | 12.49 | 58.86 | 7.27 | 12.47 |
| 46 | 140–141 | $C_{12}H_{18}N_2O_3$ | 65.43 | 7.32 | 12.72 | 65.74 | 7.24 | 12.63 |
| 47 | 97.2–98.1 | $C_{15}H_{24}N_2O_2$ | 68.15 | 9.15 | 10.6 | 68.18 | 9.28 | 10.55 |
| 48 | 101.6–101.9 | $C_{13}H_{20}N_2O_2$ | 66.07 | 8.53 | 11.85 | 66.14 | 8.7 | 11.87 |
| 49 | 68.4–69.2 | $C_{16}H_{26}N_2O_2$ | 69.03 | 9.41 | 10.06 | 68.88 | 9.51 | 10.05 |
| 50 | 69.6–70.5 | $C_{15}H_{22}N_2O_4$ | 61.21 | 7.53 | 9.52 | 61.16 | 7.43 | 9.52 |
| 51 | 141–142 | $C_{14}H_{20}N_2O_2$ | 67.72 | 8.12 | 11.28 | 67.24 | 7.84 | 11.22 |
| 52 | 93.4–94.3 | $C_{15}H_{24}N_2O_2$ | 68.15 | 9.15 | 10.6 | 68.17 | 8.89 | 10.6 |
| 53 | 103.7–104.8 | $C_{19}H_{32}N_2O_2$ | 72.21 | 10.06 | 8.74 | 71.38 | 9.85 | 8.78 |

Compound 54

1-Hydroxy-1-(2-methylpropyl)-3-phenylurea

Part A

O-Benzylhydroxylamine hydrochloride (25 g, 0.16 mole) and a suspension of sodium carbonate (18 g, 0.17 mole) in water (150 mL) were added to a solution of di-tert-butyldicarbonate (37 g, 0.17 mole) in dioxane (150 mL). The resulting white suspension was allowed to stir at ambient temperature overnight then it was partially evaporated under vacuum at 50° C. to remove most of the dioxane. The residue was acidified to pH=4 by the addition of citric acid then extracted twice with diethyl ether. The extracts were combined and concentrated under vacuum to provide 36 g of tert-butyl N-benzyloxycarbamate as a yellow oil.

Part B

Sodium hydride (0.97 g of 80% in mineral oil, 32 mmol) was added to a solution of tert-butyl N-benzyloxycarbamate (6.53 g, 29 mmol) in N,N-dimethylformamide (45 mL). A gas evolved and the mixture was stirred for 20 minutes. Isobutyl bromide (3.5 mL, 32 mmol) was added and the reaction mixture was heated at 70° C. for 1.5 hr. The reaction was quenched with water (about 50 mL) then extracted twice with diethyl ether. The extracts were combined, washed with water (5 small portions), dried over magnesium sulfate and then concentrated under vacuum to provide 7.63 g of tert-butyl N-benzyloxy-N-(2-methylpropyl)carbamate as a faintly brown oil.

Part C

Trifluoroacetic acid (21 mL, 270 mmol) was added in a single portion to a solution of tert-butyl N-benzyloxy-N-(2-methylpropyl)carbamate (7.6 g, 27 mmol) in methylene chloride (21 mL). A spontaneous reflux occurred. The reaction mixture was stirred without external heating for 20 minutes and then concentrated under vacuum at 45° C. Saturated aqueous sodium bicarbonate was added to the residue followed by a quantity of solid sodium bicarbonate sufficient to bring the pH of the reaction mixture up to a value of 9. The mixture was extracted twice with methylene chloride. The extracts were combined, dried over magnesium sulfate then concentrated under vacuum to provide 4.9 g of N-benzyloxy-N-(2-methylpropyl)amine as an oil.

Part D

Phenyl isocyanate (3.2 g, 27 mmol) was added via pipette to a solution of N-benyloxy-N-(2-methylpropyl)amine (4.8 g, 27 mmol) in methylene chloride (30 mL). The reaction mixture was allowed to stir at ambient temperature for 3 days. The solvent was removed under vacuum. The residue was purified by column chromatography (silica gel; 1:9 ethyl acetate:hexanes) to provide 6.2 g of 1-benzyloxy-1-(2-methylpropyl)-3-phenylurea as a white crystalline solid, m.p. 85°–87° C. Analysis: Calculated for $C_{18}H_{22}N_2$: %C, 72.46; %H, 7.43; %N, 9.39; Found: %C, 72.53; %H, 7.51; %N, 9.44.

Part E

Ammonium formate (6.9 g, 110 mmol) was added to a solution of 1-benzyloxy-1-(2-methylpropyl)-3-phenylurea (6.0 g, 20 mmol) in ethanol (85 mL). After 20 minutes, 10% palladium on carbon (2 g) was added and the reaction mixture was stirred at ambient temperature for 2 hours. The reaction mixture was filtered through a layer of Celite™ filter agent. The filtrate was evaporated to provide 5.4 g of a white solid. This material was recrystallized from ethyl acetate/hexanes to provide 2.35 g of the desired product as a waxy white solid, m.p. 119.3°–122.0° C. Analysis: Calculated for $C_{11}H_{16}N_2O_2$: %C, 63.44; %H, 7.74; %N, 13.45; Found: %C, 63.39; %H, 7.78; %N, 13.43.

Compounds 55–56

Using the general method of Compound 54 Part B, tert-butyl N-benzyloxycarbamate was reacted with compounds of Formula RBr to provide intermediates of Formula VII. Using the general method of Compound 54 Part C, the intermediates of Formula VII were treated with trifluoracetic acid to provide substituted O-benzylhydroxylamines of Formula VIII. Using the general method of Compound 54 Part D, phenyl isocyanate was reacted with the substituted O-benzylhydroxylamines of Formula VIII to provide the substituted ureas of Formula VI (n=0). Using the general method of Compound 54, Part E, the intermediates of Formula VI was debenzylated to provide the compounds of Formula I shown in Table 9. The melting points and elemental analyses are shown in Table 10.

TABLE 9

| Compound Number | Compound of Formula I M = H; n = 0; R" = H; R = |
| --- | --- |
| 55 | propyl |
| 56 | pentyl |

TABLE 10

| Compound Number | m.p. (°C.) | Formula | Calculated %C | %H | %N | Found %C | %H | %N |
|---|---|---|---|---|---|---|---|---|
| 55 | 91.6–94.5 | $C_{10}H_{14}N_2O_2$ | 61.84 | 7.27 | 14.42 | 61.74 | 7.19 | 14.3 |
| 56 | 98.4–98.7 | $C_{12}H_{18}N_2O_2$ | 64.84 | 8.16 | 12.6 | 64.94 | 8.06 | 12.61 |

Compound 57

3-(4-Butylphenyl)-1-hydroxy-1-pentylurea

Part A

Diethyl ether (10 mL) was added to a suspension of O-benzylhydroxylamine hydrochloride (0.82 g, 5.1 mmol) in water (1 mL). A solution of sodium hydroxide (0.23 g, 5.8 mmol) in water (1 mL) was added and the mixture was stirred for several minutes. The aqueous layer was removed by pipette and extracted with diethyl ether (3 mL). The ether extract was added to the reaction flask. 4-Butylphenyl isocyanate (0.90 g, 5.1 mole) was added to the reaction flask via pipette in a single portion. A mild reflux occurred. The reaction mixture was allowed to stir at ambient temperature for 15 minutes then purified by flash chromatography (silica gel; 1:4 ethyl acetate:hexanes) to provide 1.25 g of 1-benzyloxy-3-(4-butylphenyl)urea as a fluffy white solid, m.p. 90.6°–91.4° C.

Part B

Sodium hydride (0.14 g of 80% in mineral oil, 4.7 mmol) was added to a solution of 1-benzyloxy-3-(4-butylphenyl)urea (1.25 g, 4.2 mmol) in N,N-dimethylformamide (5 mL). The reaction mixture was heated briefly on a steam bath under a nitrogen atmosphere. The reaction mixture was allowed to cool to ambient temperature then 1-bromopentane (0.63 g, 4.2 mmol) was added. The reaction mixture was heated at 90° C. overnight. The reaction mixture was cooled to ambient temperature, diluted with water and then extracted with diethyl ether. The organic layer was washed with water, dried with magnesium sulfate and then concentrated to provide 1.47 g of crude product as a brown oil. This material was purified by flash chromatography (silica gel; 1:19 ethyl acetate:hexanes) to provide 0.96 g of 1-benzyloxy-3-(4-butylphenyl)-1-pentylurea as an oil.

Part C

Ammonium formate (1.0 g, 16 mmol) was added to a solution of 1-benzyloxy-3-(4-butylphenyl)-1-pentylurea (0.89 g, 2.4 mmol) in ethanol (10 mL). After 2 minutes, 10% palladium on carbon (300 mg) was added and the reaction was allowed to stir at ambient temperature for 1 hour. The reaction mixture was filtered to remove the catalyst and the flitrate was concentrated under vacuum at 50° C. The residue was purified by flash chromatography (silica gel; 1:9 ethyl acetate:hexanes) to provide 0.59 g of the desired product as an off-white solid, m.p. 69.3°–70.2° C. Analysis: Calculated for $C_{16}H_{26}N_2O_2$: %C, 69.03; %H, 9.41; %N, 10.06; Found: %C, 69.43; %H, 9.10; %N, 9.93.

Compound 58

1-Hydroxy-1-(2-methylpropyl)-3-[3-(methylthio)phenyl]urea

Part A

Ammonium formate (7.9 g, 125 mmol) and 10% palladium on carbon (2 g) were added to a solution of tert-butyl-N-benzyloxy-N-(2-methylpropyl)carbamate (Compound 54 Part B, 6.27 g, 22.4 mmol) in ethanol (100 mL). The reaction mixture was stirred at ambient temperature for 5 hours then concentrated under vacuum at 50° C. The residue was taken up in methylene chloride, washed with water, dried with magnesium sulfate and then concentrated to provide 4.2 g of tert-butyl N-hydroxy-N-(2-methylpropyl)carbamate as a yellow oil.

Part B

Using the general method of Compound 54 Part C, tert-butyl N-hydroxy-N-(2-methylpropyl)carbamate (4.2 g, 22 mmol) was reacted with trifluoroacetic acid (8.5 mL, 110 mmol) to provide 2.0 g of N-(2-methylpropyl)hydroxylamine as an oil.

Part C

Using the general method of Compound 54 Part D, 3-(methylthio)phenyl isocyanate (3.6 g, 22 mmol) was reacted with N-(2-methylpropyl)hydroxylamine (2.0 g, 22 mmol) to provide 1.48 g of the desired product as a white solid, m.p. 122.8°–124.9° C. Analysis: Calculated for $C_{12}H_{18}N_2O_2S$: %C, 56.67; %H, 7.13; %N, 11.01; Found: %C, 56.64; %H, 6.88; %N, 10.77.

Compound 59

1-Hydroxy-1-methyl-3-[3-(methylsulfonyl)phenyl]urea

Part A

Sodium hydride (0.48 g of 80% in mineral oil, 16 mmol) was added to a solution of tert-butyl N-benzyloxycarbamate (Compound 54 Part A, 3 g, 13 mmol) in N,N-dimethylformamide (25 mL). The reaction mixture was stirred for 20 minutes then iodomethane (1.1 mL, 18 mmol) was added dropwise with cooling in an ice bath. The resulting suspension was stirred at ambient temperature under a nitrogen atmosphere overnight. The reaction mixture was quenched with water (50 mL) then extracted with diethyl ether (150 mL). The organic layer was washed with water (5×50 mL), dried over magnesium sulfate then concentrated to provide 3.1 g of tert-butyl N-benzyloxy-N-methylcarbamate as a yellow oil.

Part B

Using the general method of Compound 54 Part C, tert-butyl N-benzyloxy-N-methylcarbamate (3.0 g, 13 mmol) was reacted with trifluoroacetic acid (10 mL, 130 mmol) to provide 1.58 g of N-benzyloxy-N-methylamine as a yellow oil.

Part C 3-(Methylthio)phenyl isocyanate (2.0 g, 12 mmol) was added dropwise to a solution of N-benzyloxy-N-methylamine (1.55 g, 11.3 mmol) in tetrahydrofuran (25 mL). The reaction mixture was stirred at ambient temperature for 2 hours then concentrated under vacuum. The residue was purified by flash chromatography (silica gel; ethyl acetate:hexanes) to provide 3.26 g of 1-benzyloxy-1-methyl-3-[3(methylthio)phenyl]urea as an oil.

Part D

3-Chloroperoxybenzoic acid (10.3 g, 30 mmol) was added to a solution of 1-benzyloxy-1-methyl-3-[3-(methylthio)phenyl]urea (4.2 g, 14 mmol) in methylene chloride (120 mL). The reaction mixture was allowed to stir at ambient temperature overnight then treated with water (50 mL) and 10% sodium hydroxide (50 mL) with vigorous stirring for 5 minutes. The organic layer was separated, dried over magnesium sulfate and concentrated to provide 4.9 g of a yellow oil. The oil was purified by flash chromatography (silica gel; ethyl acetate:hexanes) to provide 4 g of 1-benzyloxy-1-methyl-3-[3-(methylsulfonyl)phenyl]urea as an off-white solid, m.p. 110.2°–110.8° C. Analysis: Calculated for $C_{16}H_{18}N_2O_4S$: %C, 57.47; %H, 5.43; %N, 8.38; Found: %C, 57.27; %H, 5.46; %N, 8.31.

Part E

Using the general method of Compound 54 Part E, 1-benzyloxy-1-methyl-3-[3-(methylsulfonyl)phenyl]urea (3.8 g, 11.4 mmol) was debenzylated to provide 1 g of the desired product as a white crystalline solid, m.p. 159.7°–160.0° C. Analysis: Calculated for $C_9H_{12}N_2O_4S$: %C, 44.26; %H, 4.95; %N, 11.47; Found: %C, 44.68; %H, 5.05; %N, 11.48.

Compound 60

1-Hydroxy-1-(1-methylethyl)-3-[3-(methylsulfonyl)phenyl]urea

Peracetic acid (0.48 g of 32 wt %, 2 mmol) was added via pipette to a solution of 1-hydroxy-1-(1-methylethyl)-3-[3-(methylthio)phenyl]urea (Compound 16, 0.48 g, 2 mmol) in a mixture of methylene chloride (5 mL) and methanol (0.5 mL). A mild reflux was observed. The reaction mixture was allowed to stir without external heating for 1.5 hours then the volatiles were removed under vacuum at 50° C. Thin layer chromatography (silica gel; ethyl acetate) of the residue showed two components. The residue was loaded onto a column of silica gel and the faster moving component was eluted using 50:50 ethyl acetate:cyclohexane to provide 60 mg of the desired product as a solid, m.p. 168.2°–169.2° C. Analysis: Calculated for $C_{11}H_{16}N_2O_4S$: %C, 48.52; %H, 5.92; %N, 10.29; Found: %C, 49.16; %H; 5.89; %N, 10.1.

Compound 61

1-Hydroxy-1-(1-methylethyl)-3-[3-(methylsulfinyl)phenyl]urea

The slower moving component from the preparation of Compound 60 was eluted using ethyl acetate to provide 200 mg of the desired compound as a solid, m.p. 134.9°–135.8° C. Analysis: Calculated for $C_{11}H_{16}N_2O_3S$: %C, 51.55; %H, 6.29; %N, 10.93; Found: %C, 51.7; %H, 6.32; %N, 10.68.

Compound 62

1-Hydroxy-1-(1-methylethyl)-3-[4-(methylsulfonyl)phenyl]urea

Peracetic acid (4.3 g of 30%, 17 mmol) was added via pipette to a solution of 1-hydroxy-1-(1-methylethyl)-3-[4-(methylthio)phenyl]urea (Compound 15, 3.5 g, 15 mmol) in a mixture of methylene chloride (50 mL) and methanol (7 mL). A mild reflux was observed. The reaction mixture was allowed to stir without external heating for 30 minutes. Thin layer chromatography (silica gel; ethyl acetate) of the reaction mixture showed that the starting material was consumed and that two new components were present. The reaction mixture was concentrated under vacuum at 65° C. to provide an off-white solid. The solid was loaded onto a column of silica gel and the faster moving component was eluted using 50:50 ethyl acetate:hexanes to provide 1.40 g of the desired product as a fluffy white solid, m.p. 163.3°–163.8° C. Analysis: Calculated for $C_{11}H_{16}N_2O_4S$: %C, 48.52; %H, 5.92; %N 10.29; Found: %C, 48.62; %H, 5.83; %N, 10.22.

Compound 63

1-Hydroxy-1-(1-methylethyl)-3-[4-(methylsulfinyl)phenyl]urea

The slower moving component from the preparation of Compound 62 was eluted using ethyl acetate to provide 1.18 g of the desired compound as a flurry white solid, m.p. 135.6°–136.0° C. Analysis: Calculated for $C_{11}H_{16}N_2O_3S$: %C, 51.55; %H, 6.29; %N, 10.93; Found: %C, 51.7; %H, 6.17; %N, 10.95.

Compound 64

1-Hydroxy-1-methyl-3-[4-(methylsulfinyl)phenyl]urea

Peracetic acid (1.7 g of 30%, 6.6 mmol) was added dropwise to a cooled (ice/water bath) solution of 1-hydroxy-1-methyl-3-[4-(methylthio)phenyl]urea (Compound 1, 1.4 g, 6.6 mmol) in a mixture of methylene chloride (25 mL) and methanol (10 mL). The solution was stirred with cooling for 15 minutes. The solvent was removed under reduced pressure at 50° C. to provide a white solid. The solid was dissolved in hot ethyl acetate/ethanol, filtered to remove particulates then diluted with ether to provide 0.8 g of the desired product as a white crystalline solid, m.p. 197.8°–198.2° C. Analysis: Calculated for $C_9H_{12}N_2O_3S$: %C, 47.36; %H, 5.3; %N, 12.27; Found: %C, 47.27; %H, 4.97; %N, 12.26.

Compound 65

1-Hydroxy-1-methyl-3-[4-(methylsulfonyl)phenyl]urea

Peracetic acid (3.4 g of 30%, 14 mmol) was added dropwise to a solution of 1-hydroxy-1-methyl-3-[4-(methylthio)phenyl]urea (Compound 1, 1.4 g, 6.6 mmol) in a mixture of methylene chloride (25 mL) and methanol (10 mL). The solution was stirred for 1 hour then the solvent was removed under reduced pressure. The residue was recrystallized twice from ethyl acetate/ethanol/ether to provide 0.39 g of the desired product as a white crystalline solid, m.p. 197.6°–198.2° C. Analysis: Calculated for $C_9H_{12}N_2O_4S$: %C, 44.26; %H, 4.95; %N, 11.47; Found: %C, 44.92; %H, 5.0; %N, 11.57.

Compound 66

1-Hydroxy-1-(1-methylethyl)-3-(3,4,5-trimethoxyphenyl)urea

A solution of N-isopropylhydroxylamine hydrochloride (1.2 g, 11 mmol) in water (5 mL) was combined with diethyl ether (35 mL) then cooled in an ice bath. A solution of sodium hydroxide (0.5 g, 12.5 mmol) in water (7 mL) was added over a 10 minute period. The reaction mixture was stirred for 10 minutes then 3,4,5-trimethoxyphenyl isocyanate (2.1 g, 10 mmol) was added as a solid. The reaction mixture was stirred at ambient temperature for 18 hours then filtered to remove a white precipitate. The filtrate was concentrated under vacuum to provide 2.1 g of the desired product as a white solid. An analytical sample was prepared by recrystallization from hexanes:ethyl acetate, m.p. 140.0°–141.0 ° C. Analysis: Calculated for $C_{13}H_{20}N_2O_5$: %C, 54.92; %H, 7.09; %N, 9.85; Found: %C, 55.12; %H, 7.06; %N, 9.77.

Compound 67

1-Hydroxy-1-(1-methylethyl)-3-(2,4,5-trimethylphenyl)urea

A solution of N-isopropylhydroxylamine hydrochloride (1.85 g, 16.5 mmol) in water (5 mL) was combined with diethyl ether (50 mL) then cooled in an ice bath. A solution of sodium hydroxide (0.72 g, 18 mmol) in water (10 mL) was added over a 10 minute period. The reaction mixture was stirred for 10 minutes then 2,4,5-trimethylphenyl isocyanate (2.42 g, 15 mmol) was added as a solid. The reaction mixture was stirred at ambient temperature for 18 hours. A white solid was isolated by filtration then recrystallized from hexanes/ethyl acetate to provide 2.4 g of the desired product as a white crystalline solid, m.p. 176.2°–176.8° C. Analysis: Calculated for $C_{13}H_{20}N_2O_2$: %C, 66.07; %H, 8.53; %N, 11.85; Found: %C, 65.85; %H, 8.35; %N, 11.68.

Compound 68

1-Hydroxy-1-(1-methylbutyl)-3-phenylurea

Part A

Using the general method of Compound 42 Part B, 2-bromopentane (2.7 mL, 21.7 mmole) was reacted with 1-benzyloxy-3-phenylurea (4.9 g, 20.1 mmole) to provide 4.26 g of 1-benzyloxy-1-(1-methylbutyl)-3-phenylurea as a yellow oil.

Part B

Using the general method of Compound 42 Part C, 1-benzyloxy-1-(1-methylbutyl)-3-phenylurea (3.89 g, 43.6 mmole) was debenzylated to provide 2.3 g of the desired product as white needles, m.p. 51.4°–52.3° C. Analysis: Calculated for $C_{12}H_{18}N_2O_2$: %C, 64.84; %H, 8.16; %N, 12.6; Found: %C, 64.62; %H, 8.1; %N, 12.61.

Compound 69

1-Hydroxy-1-(1-methylpropyl)-3-phenylurea

Part A

Using the general method of Compound 42 Part B, 2-bromobutane (2.37 mL, 21.7 mmole) was reacted with 1-benzyloxy-3-phenylurea (4.87 g, 20.1 mmole) to provide 2.2 g of 1-benzyloxy-1-(1-methylpropyl)-3-phenylurea.

Part B

Using the general method of Compound 42 Part C, 1-benzyloxy-1-(1-methylpropyl)-3-phenylurea (2 g, 6.7 mmole) was debenzylated to provide about 0.7 g of the desired product as a white crystalline solid, m.p. 111°–112° C. Analysis: Calculated for $C_{11}H_{16}N_2O_2$: %C, 63.44; %H, 7.74; %N, 13.45; Found: %C, 62.89; %H, 7.71; %N, 13.24.

Compound 70

1-Hydroxy-1-(1-propylbutyl)-3-phenylurea

Part A

Using the general method of Compound 42 Part B, 4-bromoheptane (5.84 g, 32.6 mmole) was reacted with 1-benzyloxy-3-phenylurea (7.3 g, 30.2 mmole) to provide about 4 g of 1-benzyloxy-1-(1-propylbutyl)-3-phenylurea.

Part B

Using the general method of Compound 42 Part C, 1-benzyloxy-1-(1-propylbutyl)-3-phenylurea (3.9 g, 11.5 mmole) was debenzylated to provide 1.8 g of the desired product as a white crystalline solid, m.p. 138.5° C. Analysis: Calculated for $C_{14}H_{22}N_2O_2$: %C, 67.17; %H, 8.86; %N, 11.19; Found: %C, 67.21; %H, 8.86; %N, 11.16.

Compound 71

1-Hydroxy-1-(1-ethylbutyl)-3-phenylurea

Part A

Using the general method of Compound 42 Part B, 3-bromohexane (4.59 mL, 32.6 mmole) was reacted with 1-benzyloxy-3-phenylurea (7.3 g, 30.2 mmole) to provide 3.4 g of 1-benzyloxy-1-(1-ethylbutyl)-3-phenylurea.

Part B

Using the general method of Compound 42 Part C, 1-benzyloxy-1-(1-ethylbutyl)-3-phenylurea (3.15 g, 9.65 mmole) was debenzylated to provide about 1.6 g of the desired product as a white powder, m.p. 117.8°–118.4° C. Analysis: Calculated for $C_{13}H_{20}N_2O_2 \cdot \frac{1}{2} H_2O$: %C, 63.65; %H, 8.63; %N, 11.42; Found: %C, 63.34; %H, 8.12; %N, 11.37.

Compound 72

1-Hydroxy-1-(1-ethylpropyl)-3-(4-phenoxyphenyl)urea

A solution of N-(1-ethylpropyl)hydroxylamine (1.13 g, 11 mmole, Compound 39, Part B) in tetrahydrofuran (30 mL) was charged with 4-phenoxyphenylisocyanate (2.1 g, 10 mmole) and maintained at ambient temperature overnight. The solvent was removed in vacuo to yield 3.2 g of the crude product as a white solid. Recrystallization from hexanes-ethyl acetate provided 1.6 g of the desired product as a white crystalline solid, m.p. 124°–125° C. Analysis: Calculated for: $C_{18}H_{22}N_2O_3$: %C, 68.77; %H, 7.05; %N, 8.91; Found: %C, 68.44; %H, 7.09; %N, 8.82.

Compound 73

1-Hydroxy-1-(1-ethylpropyl)-3-(3,5-bis(trifluoromethyl)phenyl)urea

Using the method of Compound 72, 3,5-bis(trifluoromethyl)phenylisocyanate (1.3 g, 5.1 mmole) was reacted with N-(1-ethylpropyl)hydroxylamine (0.58 g, 5.6 mmole) to provide 160 mg of the desired product as a white crystalline solid, m.p. 115°–116° C. Analysis: Calculated for:

$C_{14}H_{16}F_6N_2O_2$: %C, 46.93; %H, 4.5; %N, 7.82; Found: %C, 46.8; %H, 4.37; %N, 7.89.

Compound 74

1-Hydroxy-1-(1-ethylpropyl)-3-methyl-3-phenylurea

Part A

Using the general method of Compound 54 Part B, 3-bromopentane (15.0 mL, 121 mmole) was reacted with tert-butyl N-benzyloxycarbamate (25.1 g, 112 mmole) to provide tert-butyl N-benzyloxy-N-(1-ethylpropyl)carbamate.

Part B

Trifluoroacetic acid (42 mL, 544 mmole) was added to a chilled (0° C.) solution of tert-butyl N-benzyloxy-N-(1-ethylpropyl)carbamate (21.6 g, 73.6 mmole) in methylene chloride (300 mL). The reaction was stirred at ambient temperature for about 18 hours then concentrated under vacuum. Saturated aqueous sodium bicarbonate (100 mL) was added to the residue followed by a quantity of solid sodium carbonate sufficient to adjust the pH of the reaction mixture to pH 9. The reaction mixture was extracted with diethyl ether (4×50 mL). The extracts were combined, dried over sodium sulfate then concentrated to provide 10.9 g of N-benzyloxy-N-(1-ethylpropyl)amine as an oil.

Part C

A tube was charged with a stir bar, N-benzyloxy-N-(1-ethylpropyl)amine (2.0 g, 10.3 mmole), tetrahydrofuran (5 mL), triethylamine (4.31 mL), N-methyl-N-phenylcarbamoyl chloride (1.75 g, 10.3 mmole), and 4-dimethylaminopyridine (1 mg). The tube was flushed with nitrogen, sealed and then heated to 130° C. After 48 hours the reaction mixture was cooled to ambient temperature and concentrated under vacuum. The residue was purified by chromatography (silica gel; 9:1 hexanes:ethyl acetate) to provide 2.0 g of 1-benzyloxy-1-(1-ethylpropyl)-3-methyl-3-phenylurea.

Part D

A mixture of 1-benzyloxy-1-(1-ethylpropyl)-3-methyl-3-phenylurea (2.0 g, 6.1 mmole), ammonium formate (1.2 g, 19 mmole), 10% palladium on carbon (0.7 g) and absolute ethanol (50 mL) was stirred at ambient temperature for 1 hour. The reaction mixture was filtered through a layer of Celite™ filter agent and the filter agent was washed with ethyl acetate. The filtrate was concentrated then purified by chromatography (silica gel; 4:1 hexanes:ethyl acetate) to provide 1.2 g of the desired product as a beige solid, m.p. 68.4°–69.1° C. Analysis: Calculated for $C_{13}H_{20}N_2O_2$: %C, 66.07; %H, 8.53; %N, 11.85; Found: %C, 65.78; %H, 8.42; %N, 11.67.

Compound 75

1-Hydroxy-1,3-dimethyl-3-phenylurea

Part A

O-Benzylhydroxylamine hydrochloride (3.0 g, 18.8 mmole) was dissolved in water (3.5 mL) then combined with diethyl ether (85 mL) followed by the addition of sodium hydroxide (0.75 g, 18.8 mmole) in water. After several minutes a solution of N-methyl-N-phenylcarbamoyl chloride (3.19 g, 18.8 mmole) in diethyl ether (25 mL) was added. A white precipitate formed. The solid was isolated by filtration then dissolved in water. The solution was diluted with saturated aqueous sodium bicarbonate and sufficient solid sodium carbonate was added to bring the pH to 9. The solution was extracted with diethyl ether (5×50 mL). The ether extracts were combined, dried and then concentrated to provide the crude product as a beige solid. The crude product was purified by silica gel chromatography (9:1 hexanes/ethyl acetate) to provide 3.1 g of 1-benzyloxy-3-methyl-3-phenylurea.

Part B

Under a nitrogen atmosphere, a flask was charged with sodium hydride (0.29 g 60% NaH in mineral oil, 7.3 mmole). The mineral oil was washed from the sodium hydride using several portions of hexanes. N,N-Dimethylformamide (60 mL) was added followed by the slow addition of a solution of 1-benzyloxy-3-methyl-3-phenylurea (1.69 g, 6.6 mmole) in N,N-dimethylformamide (40 mL). Hydrogen evolution was observed. After about 30 minutes methyl iodide (480 μL) was added then the reaction was stirred at ambient temperature for about 1.5 hours. The reaction was quenched with water (about 65 mL). The aqueous layer was salted then extracted with diethyl ether (4×80 mL). The extracts were combined, dried over magnesium sulfate then concentrated to provide crude product as an oil. The crude product was purified by silica gel chromatography (5:1 hexanes:ethyl acetate) to provide 1.54 g of 1-benzyloxy-1,3-dimethyl-3-phenylurea.

Part C

Using the general method of Compound 74 Part D, 1-benzyloxy-1,3-dimethyl-3-phenylurea (1.5 g, 5.6 mmole) was debenzylated to provide 0.8 g of the desired product as an off-white powder, m.p. 87.8°–88.8° C. Analysis: Calculated for $C_9H_{12}N_2O_2$: %C, 59.99; %H, 6.71; %N, 15.54; Found: %C, 60.01; %H, 6.5; %N, 15.56.

Compound 76

1-Hydroxy-1-(1-ethylpropyl)-3-(2-phenoxyphenyl)urea

A solution of 2-phenoxybenzoic acid (2.63 g, 12.3 mmole), triethylamine (1.8 mL, 13 mmole) and diphenylphosphoryl azide (2.9 mL, 13.5 mmole) in toluene (50 mL) was heated at 95° C. for 2 hours. The reaction was cooled to ambient temperature and N-(1-ethylpropyl)hydroxylamine (1.9 g, 18.4 mmole) was added as a solid. The reaction was maintained overnight then concentrated under vacuum to provide the crude product as a yellow oil. The residue was partitioned between diethyl ether (100 mL) and water (100 ml). The fractions were separated and the aqueous fraction was extracted with additional portions of diethyl ether (3×50 mL). The combined organic fractions were dried over sodium sulfate, filtered and concentrated. The residue was recrystallized from hexanes\ethyl acetate to provide 2.3 g of the desired product as a white crystalline solid, m.p. 141.2°–141.8° C. Analysis: Calculated for $C_{18}H_{22}N_2O_3$: %C, 68.77; %H, 7.05; %N, 8.91; Found: %C, 68.23; %H, 6.8; %N, 8.89.

Compound 77

1-Hydroxy-1-(1-ethylpropyl)-3-(3-phenoxyphenyl)urea

Using the method of Compound 76, 3-phenoxybenzoic acid (3.47 g, 16 mmole) was converted to the corresponding isocyanate then reacted with N-(1-ethylpropyl)hydroxylamine (2.5 g, 24 mmole) to provide 3.2 g of the desired product as white plates, m.p. 110.6°–111.4° C. Analysis: Calculated for $C_{18}H_{22}N_2O_3$: %C, 68.77; %H, 7.05; %N, 8.91; Found: %C, 68.4; %H, 6.67; %N, 8.89.

Compound 78

1-Hydroxy-1-(1-ethylpropyl)-3-(4-benzylphenyl)urea

Using the method of Compound 76, 4-benzylbenzoic acid (1.93 g, 9 mmole) was converted to the corresponding isocyanate then reacted with N-(1-ethylpropyl)hydroxylamine (1.4 g, 14 mmole) to provide 1.9 g of the desired product as off-white crystals, m.p. 132.5°–134.1° C. Analysis: Calculated for $C_{19}H_{24}N_2O_2$: %C, 73.05; %H, 7.74; %N, 8.97; Found: %C, 72.82; %H, 7.82; %N, 8.79.

Compound 79

1-Hydroxy-1-(1-ethylpropyl)-3-(4-benzoylphenyl)urea

Using the method of Compound 76, 4-benzoylbenzoic acid (1.47 g, 6.5 mmole) was converted to the corresponding isocyanate then reacted with N-(1-ethylpropyl)hydroxylamine (1.0 g, 10 mmole) to provide 0.58 g of the desired product as white crystals, m.p. 156°–157° C. Analysis: Calculated for $C_{19}H_{22}N_2O_3$: %C, 69.92; %H, 6.79; %N, 8.58; Found: %C, 69.7; %H, 6.61; %N, 8.64.

Compound 80

1-Hydroxy-1-(1-ethylpropyl)-3-(4-benzyloxyphenyl)urea

Part A

A mixture of methyl 4-hydroxybenzoate (3.0 g, 19.7 mmole), potassium carbonate (2.8 g, 20.2 mole) and N,N-dimethylformamide (40 mL) was stirred at 70° C. for 2 hours. Benzyl bromide (2.38 mL, 20 mmole) was added and the reaction was maintained for an additional 18 hours. The mixture was cooled to ambient temperature and dissolved into water (400 mL). The aqueous phase was extracted with ethyl acetate (3×100 mL). The combined organic fractions were dried over magnesium sulfate, filtered and concentrated to provide 4.5 g of methyl 4-benzyloxybenzoate as a white powder, m.p. 96°–97° C.

Part B

A solution of methyl 4-benzyloxybenzoate (4.2 g, 17.3 mmole) and sodium hydroxide (15 mL of 2N) in methanol (200 mL) was heated at reflux for 24 hours. The methanol was removed under vacuum and water (200 mL) was added to the resulting residue. The mixture was acidified to pH 3 by the dropwise addition of concentrated hydrochloric acid. The resulting precipitate was isolated by filtration, washed with cold water and dried to provide 3.1 g of 4-benzyloxybenzoic acid as a white powder, m.p. 186°–187° C.

Part C

Using the general method of Compound 76, 4-benzoylbenzoic acid (2.0 g, 8.8 mmole) was converted to the corresponding isocyanate then reacted with N-(1-ethylpropyl)hydroxylamine (1.4 g, 13.6 mmole) to provide 1.5 g of the desired product as a white powder, m.p. 156°–157° C. Analysis: Calculated for $C_{19}H_{24}N_2O_3$: %C, 69.49; %H, 7.37; %N, 8.53; Found: %C, 69.52; %H, 7.14; %N, 8.44.

Compound 81

1-Hydroxy-1-(1-ethylpropyl)-3-[4-(cyclohexylmethoxy)phenyl]urea

Part A

Using the general method of Compound 80 Part A, methyl 4-hydroxybenzoate (3.0 g, 19.7 mmole) was reacted with cyclohexylmethyl bromide (2.8 mL, 20.1 mmole) to provide 3.1 g of methyl 4-cyclohexylmethoxybenzoate as a white crystalline solid, m.p. 62°–63° C.

Part B

Using the general method of Compound 80 Part B, methyl 4-cyclohexylmethoxy benzoate (2.9 g, 11.7 mmole) was hydrolyzed to provide 1.5 g of 4-(cyclohexylmethoxy)benzoic acid as a white powder, m.p. 209°–210° C.

Part C

Using the general method of Compound 76, 4-(cyclohexylmethoxy)benzoic acid (1.0 g, 4.3 mmole) was convened to the isocyanate then reacted with N-(1-ethylpropyl)hydroxylamine (0.66 g, 6.4 mmole) to provide 0.7 g of the desired product as a white crystalline solid, m.p. 132°–133.5° C. Analysis: Calculated for $C_{19}H_{30}N_2O_3$: %C, 68.23; %H, 9.04; %N, 8.38; Found: %C, 67.89; %H, 9.03; %N, 8.44.

Compound 82

1-Hydroxy-1-(1-ethylpropyl)-3-[4-(3-phenylpropyloxy)phenyl]urea

Part A

Using the general method of Compound 80 Part A, methyl 4-hydroxybenzoate (3.0 g, 19.7 mmole) was reacted with 1-bromo-3-phenylpropane (3.1 mL, 20.4 mmole) to provide 4.8 g of methyl 4-(3-phenylpropyloxy)benzoate as a white crystalline solid, m.p. 61.0°–61.5° C.

Part B

Using the general method of Compound 80 Part B, methyl 4-(3-phenylpropyloxy)benzoate (4.5 g, 16.7 mmole) was hydrolyzed to provide 4.1 g of 4-(3-phenylpropyloxy)benzoic acid as a white powder, m.p. 165°–166° C.

Part C

Using the general method of Compound 76, 4-(3-phenylpropyloxy)benzoic acid (2.0 g, 7.8 mmole) was converted to the isocyanate then reacted with N-(1-ethylpropyl)hydroxylamine (1.2 g, 11.6 mmole) to provide 0.8 g of the desired product as a white crystalline solid, m.p. 135°–136° C. Analysis: Calculated for $C_{21}H_{28}N_2O_3$: %C, 70.76; %H, 7.92; %N, 7.86; Found: %C, 70.76; %H, 7.96; %N, 7.84.

Compound 83

1-Hydroxy-1-(1-ethylpropyl)-3-(biphenyl-4-yl)urea

Using the general method of Compound 76, 4-biphenylcarboxylic acid (1.3 g, 6.5 mmole) was converted to the isocyanate then reacted with N-(1-ethylpropyl)hydroxylamine (1.0 g, 10 mmole) to provide 0.54 g of the desired product as a white crystalline solid, m.p. 183°–184° C. Analysis: Calculated for $C_{18}H_{22}N_2O_2$: %C, 72.46; %H, 7.43; %N, 9.39; Found: %C, 72.38; %H, 7.15; %N, 9.26.

Compound 84

1-Hydroxy-1-(1-ethylpropyl)-3-(4'-octyloxybiphenyl-4-yl)urea

Using the general method of Compound 76, 4'-octyloxy-4-biphenylcarboxylic acid (3.26 g, 10 mmole) was converted to the isocyanate then reacted with N-(1-ethylpropyl)hydroxylamine (1.4 g, 13.5 mmole) to provide 2.0 g of the desired product as a light tan crystalline solid, m.p. 151°–152.5° C. Analysis: Calculated for $C_{26}H_{38}N_2O_3$: %C, 73.20; %H, 8.98; %N, 6.57; Found: %C, 73.19; %H, 9.01; %N, 6.50.

Compound 85

1-Hydroxy-1-(1-ethylpropyl)-3-(3-cyclopentyloxy-4-methoxyphenyl)urea

Part A

Potassium carbonate (27.6 g, 0.20 mole) was added to a solution of cyclopentyl bromide (26.4 g, 0.18 mole) and isovanillin (25.8 g, 0.17 mole) in N,N-dimethyl formamide (80 mL). The resulting suspension was stirred at ambient temperature for 1 week, then diluted with water (about 500 mL) and extracted with diethyl ether (2×300 mL). The combined ether extracts were washed with water (5×150 mL), 10% sodium hydroxide (3×50 mL), and water (2×100 mL), then dried over magnesium sulfate and concentrated under vacuum to provide 27.5 g of 3-cyclopentyloxy-4-methoxybenzaldehyde as a viscous yellow oil.

Part B

A suspension of 3-cyclopentyloxy-4-methoxybenzaldehyde (19.8 g, 0.09 mole) and sulfamic acid (11.4 g, 0.12 mole) in 80% acetic acid (155 mL) was stirred while a solution of 80% sodium chlorite in water (43 mL) was slowly added. The reaction temperature was maintained at about 20° C. with an ice bath. The resulting yellow mixture was stirred at 20° C. for 1.5 hours, diluted with water (160 mL) and then stirred for 10 minutes. A white solid was isolated by filtration, washed with water and dried in a vacuum oven at 60° C. to provide 19.3 g of 3-cyclopentyloxy-4-methoxybenzoic acid.

Part C

Using the general method of Compound 76, 3-cyclopentyloxy-4-methoxybenzoic acid (2.36 g, 10 mmole) was converted to the corresponding isocyanate then reacted with N-(1-ethylpropyl)hydroxylamine (1.4 g, 13.5 mmole) to provide 1.4 g of the desired product as white needles, m.p. 127.0°–128.0° C. Analysis: Calculated for $C_{18}H_{28}N_2O_4$: %C, 64.26; %H, 8.39; %N, 8.33; Found: %C, 64.21; %H, 8.2; %N, 8.23.

EXAMPLE 1

5-LIPOXYGENASE INHIBITION IN HUMAN LEUKOCYTES

The test method described below measures the ability of compounds to inhibit 5-lipoxygenase activity in human leukocytes.

Blood Cell Preparation

Whole human blood is collected by venipuncture into EDTA (1.4 mL of 0.25M per 60 mL of whole blood). The red blood cells are sedimented with a 6% dextran/0.9% sodium chloride solution at a ratio of 25 mL whole blood to 15 mL dextran solution. The blood/dextran combination is mixed by inversion and the red blood cells are allowed to settle out for 45 minutes at ambient temperature. The plasma/dextran supernatant is removed then centrifuged at ambient temperature at 3000 rpm for 10 minutes. The plasma/dextran supernatant is removed and the cells are resuspended in 10 mL of the plasma-dextran solution. The cell suspension is combined with 20 mL of water, mixed for 1.5 minutes then immediately combined with 10 mL of 3.6% sodium chloride, mixed and centrifuged at ambient temperature at 3000 rpm for 10 minutes. The pellet is washed with 40 mL of Tris buffer (5.55 mM dextrose, 15.36 mM Tris base, 136.9 mM sodium chloride with pH 7.3–7.4) then centrifuged at 3000 rpm for 10 minutes. The pellet is then resuspended into Tris buffer containing 1 mM calcium chloride to provide approximately $1.0 \times 10^7$ cells/mL.

Compound Preparation

Compounds are dissolved in dimethyl sulfoxide. Compounds are tested at concentrations of 100, 33, 11, 3.7, 1.2 and 0.41 µM. Each concentration is tested in duplicate.

Incubation

A 15 µL portion of Tris buffer containing 1 mM calcium chloride is added to each well of a 96 well microtiter plate. A 1 µL portion of drug solution or vehicle (dimethyl sulfoxide) is added to each well followed by the addition of an 75 µL portion of the cell suspension. The plates are gently mixed then allowed to stand at ambient temperature for 10 minutes. A 10 µL portion of 30 µM A23187 Calcium Ionophore (prepared by dissolving the ionophore in DMSO and then diluting 1:80 into the Tris buffer) is added to each well except the wells that contain the blanks (The blank wells measure the level of $LTC_4$ production in the absence of A23187.). The plates are gently mixed then incubated at 37° C. for 10 minutes.

Separation

Following incubation the plates are centrifuged at 2000 rpm for 1.5 minutes and the supernatant is removed as quickly as possible to stop the reaction. The supernatants are frozen at −20° C. until they are assayed.

Analysis/Calculations

The supernatants are assayed for the presence of Leukotriene $C_4$ by radioimmunoassay which is performed according to the manufacturer's (Advanced Magnetics; Cambridge, Mass.) instructions. Inhibition of 5-lipoxygenase activity is calculated as the ratio of the amount of $LTC_4$ formed in the presence ($LTC_4$+cpd) and absence ($LTC_4$ no cpd) of compound according to the following equation.

$$\% \text{ Inhibition} = \frac{(LTC_4 \text{ no cpd}) - (LTC_4 + cpd)}{(LTC_4 \text{ no cpd})} \times 100$$

$IC_{50}$ values (concentrations of compound producing 50% enzyme inhibition) are calculated by linear regression analysis of percentage inhibition versus log compound concentration plots.

A number of the compounds that are useful in the practice of the method of the invention were tested. The results are shown in Table 11 below.

TABLE 11

| 5-Lipoxygenase Inhibition in Human Leukocytes | |
|---|---|
| Compound | $IC_{50}$ (µM) |
| 1 | 0.083 |
| 2 | 0.040 |
| 3 | 0.082 |
| 4 | 0.027 |
| 5 | 0.42 |
| 6 | 0.07 |
| 7 | 0.28 |
| 8 | 0.68 |
| 9 | 0.08 |
| 10 | 0.02 |
| 11 | 0.049 |
| 16 | 0.008 |
| 17 | 0.043 |
| 18 | 0.21 |
| 19 | 0.10 |
| 20 | 0.70 |
| 21 | 0.23 |
| 22 | 0.74 |
| 23 | 0.15 |
| 24 | 0.2 |

TABLE 11-continued

5-Lipoxygenase Inhibition in Human Leukocytes

| Compound | IC$_{50}$ (μM) |
|---|---|
| 25 | 0.13 |
| 26 | >10 |
| 31 | 0.006 |
| 33 | 9.1 |
| 34 | 0.46 |
| 43 | 0.03 |
| 44 | 0.01 |
| 54 | 0.094 |
| 55 | 0.052 |
| 58 | 0.002 |
| 59 | 1.1 |

EXAMPLE 2

IN VITRO HUMAN WHOLE BLOOD LEUKOTRIENE B$_4$ INHIBITION

The test method described below measures the ability of compounds to inhibit the production of Leukotriene B$_4$ in whole human blood.

Blood Cell Preparation

Whole human blood is collected by venipuncture into a 60 cc syringe containing 100 units of heparin.

Compound Preparation

Compounds are dissolved in dimethyl sulfoxide. Compounds are tested at concentrations of 100, 33, 11, 3.7, 1.2 and 0.41 μM. Each concentration is tested in duplicate.

Incubation

Aliquots (1 μL) of compound solution are added to 1 mL polyethylene tubes followed by the addition of a 500 μL portion of heparinized blood. The tubes are mixed thoroughly then allowed to preincubate at ambient temperature for 15 minutes. A 25 μL portion of 1 mM Calcium Ionophore A23187 in dimethyl sulfoxide/Tris buffer is added to the tubes. The tubes are mixed thoroughly then incubated at 37° C. for 30 minutes.

Separation

The tubes are centrifuged at 2000 rpm for 10 minutes. 100 μL portions of plasma are transferred to 1 mL polyethylene tubes containing 400 μL portions of methanol. The tubes are vortexed then frozen at −20° C. overnight.

Analysis/Calculations

The tubes are centrifuged for 10 minutes then 100 μL portions of methanol supernatant are transferred to a 96 well microtiter plate. 10 μL portions are transferred from this plate to a 96 well assay plate. Methanol dilutions of LTB$_4$ standard curve are added to the assay plate. 10 μL portions of blank methanol/plasma supernatant are added to each standard curve well. The assay plate is vacuum dried at ambient temperature. The radioimmunoassay buffer is added, the plate is bath-sonicated for 5 minutes then assayed according to the manufacturer's (Advanced Magnetics; Cambridge, Mass.) instructions. Inhibition of LTB$_4$ production is calculated as the ratio of the amount of LTB$_4$ formed in the presence (LTB$_4$+cpd) and absence (LTB$_4$ no cpd) of compound according the equation below.

$$\% \text{ Inhibition} = \frac{(\text{LTB}_4 \text{ no cpd}) - (\text{LTB}_4 + \text{cpd})}{(\text{LTB}_4 \text{ no cpd})} \times 100$$

IC$_{50}$ values (concentration of compound producing a 50% inhibition of LTB$_4$ production) are calculated by linear regression analysis of percentage inhibition versus log compound concentration plots.

A number of the compounds that are useful in the practice of the method of the invention were tested. The results are shown in Table 12 below where IA indicates that the compound was inactive in this particular test.

TABLE 12

In Vitro Human Whole Blood Leukotriene B$_4$ Inhibition

| Compound | IC$_{50}$ (μM) |
|---|---|
| 1 | 0.38 |
| 2 | 0.010 |
| 3 | 0.07 |
| 4 | 0.008 |
| 5 | 0.2 |
| 6 | 0.079 |
| 7 | 0.092 |
| 8 | 0.17 |
| 9 | 0.4 |
| 10 | 0.51 |
| 11 | 0.37 |
| 12 | 0.19 |
| 13 | 0.3 |
| 14 | 0.2 |
| 15 | 0.27 |
| 16 | 0.4 |
| 17 | 0.4 |
| 18 | 0.9 |
| 19 | 0.8 |
| 20 | 0.9 |
| 21 | 1.1 |
| 22 | 1.2 |
| 23 | 0.1 |
| 24 | 0.09 |
| 25 | 0.2 |
| 26 | 2.3 |
| 27 | 0.08 |
| 28 | 2.5 |
| 29 | 0.56 |
| 30 | 0.2 |
| 31 | 1.1 |
| 32 | 1.4 |
| 33 | IA |
| 34 | >10 |
| 36 | 0.3 |
| 37 | 0.2 |
| 38 | 5.7 |
| 39 | 1.1 |
| 40 | 1.4 |
| 41 | 2.7 |
| 42 | 0.93 |
| 43 | 0.3 |
| 44 | 0.38 |
| 45 | 0.32 |
| 46 | 0.6 |
| 47 | 0.9 |
| 48 | 1.5 |
| 49 | 1.3 |
| 50 | 0.2 |
| 51 | 0.6 |
| 52 | 0.7 |
| 53 | 0.6 |
| 54 | 0.1 |
| 55 | 0.6 |
| 56 | 0.11 |
| 57 | 0.067 |
| 58 | 2.1 |
| 59 | 0.3 |
| 60 | 0.7 |
| 61 | 2.1 |
| 62 | 0.5 |
| 63 | 0.7 |
| 64 | 3.8 |
| 65 | 1.4 |
| 66 | 16.1 |
| 67 | 0.9 |
| 68 | 0.6 |
| 69 | 0.6 |
| 70 | 2.8 |

TABLE 12-continued

In Vitro Human Whole Blood Leukotriene $B_4$ Inhibition

| Compound | $IC_{50}$ (μM) |
|---|---|
| 71 | 1.9 |
| 72 | 0.3 |
| 73 | 33.1 |
| 74 | 7.7 |
| 75 | 1.4 |
| 76 | 7.3 |
| 77 | 1.1 |
| 78 | 2.9 |
| 79 | 6.4 |
| 80 | 3.9 |
| 81 | 8.5 |
| 82 | 2.8 |
| 83 | 1.8 |

EXAMPLE 3

IN VITRO MOUSE PERITONEAL MACROPHAGE LEUKOTRIENE $C_4$ INHIBITION

The test method described below measures the ability of compounds to inhibit the production of Leukotriene $C_4$ in mouse peritoneal macrophages.

Cell Preparation

Mice (female, CD-1, weighing 25 g) are euthanized by exposure to carbon dioxide. The peritoneal cavity is exposed by peeling back the abdominal skin. A 5 mL portion of media (M199 containing 1% fetal bovine serum, 100 units/mL of penicillin, 100 μg/mL of streptomycin, 20 units/mL of heparin and no glutamine) is injected into the exposed peritoneal cavity of each mouse. The lavage fluid is removed and pooled to yield approximately 1×10⁶ macrophages/mL. A 2 mL portion of lavage fluid is added to each well of a 24 well sterile multi-dish and the macrophages are allowed to adhere to the plate for 2 hours at 37° C. in a 5% carbon dioxide atmosphere. The media is removed and each well is washed with 2 mL of phosphate buffered saline (PBS). A 1 mL portion of media, without heparin, but containing 5 μCi/mL of 3H-myoinositol is added to each well and the plates are incubated overnight at 37° C. in a 5% carbon dioxide atmosphere. The media is removed and the cells are washed twice with 2 mL portions of PBS. A 1 mL portion of Puck's saline formulation A containing 1 mM calcium chloride, 1 mM magnesium chloride and 10 mM lithium chloride is added to each well. (The Puck's formulation is made first as a 10× solution which contains 4 g of potassium chloride, 80 g of sodium chloride and 10 g of glucose per liter. The Puck's saline formulation A is made using 10 mL of the 10× Puck's formulation, 0.47 mL of 7.5% sodium bicarbonate and 2 mL of 1M N-2-hydroxyethylpiperazine-N'-2-ethanesulfonic acid per 100 mL.)

Compound Preparation

Compounds are dissolved in dimethyl sulfoxide. Compounds are tested at concentrations of 10, 1 and 0.1 μM. Each concentration is tested in duplicate.

Incubation

A 1 μL portion of compound solution or vehicle (DMSO) is added to each well and the plates are incubated for 15 minutes at 37° C. in a 5% carbon dioxide atmosphere. Zymosan is then added to provide a final concentration of 50 μg/mL in each well and the plate is incubated for 1 to 2 hours at 37° C. in a 5% carbon dioxide atmosphere.

Separation

Following incubation 200 μL portions of media are transferred to 12×75 mm tubes. The tubes are either assayed immediately or stored at −20° C. until they can be assayed.

Analysis/Calculations

The media is assayed for the presence of Leukotriene $C_4$ by radioimmunoassay which is performed according to the manufacturer's (Advanced Magnetics; Cambridge, Mass.) instructions. Inhibition of $LTC_4$ production is calculated as the ratio of the amount of $LTC_4$ formed in the presence ($LTC_4$+cpd) and absence ($LTC_4$ no cpd) of compound according to the equation below.

$$\% \text{ Inhibition} = \frac{(LTC_4 \text{ no cpd}) - (LTC_4 + \text{cpd})}{(LTC_4 \text{ no cpd})} \times 100$$

$IC_{50}$ values (concentration of compound producing a 50% inhibition of $LTC_4$ production) are calculated by linear regression analysis of percentage inhibition versus log compound concentration plots.

A number of the compounds that are useful in the practice of the method of the invention were tested. The results are shown in Table 13 below.

TABLE 13

IN VITRO MOUSE PERITONEAL MACROPHAGE LEUKOTRIENE $C_4$ INHIBITION

| Compound | $IC_{50}$ (μM) |
|---|---|
| 1 | <1 |
| 5 | 0.2 |
| 6 | <0.1 |
| 7 | <1 |
| 8 | 0.4 |
| 9 | 0.7 |
| 10 | <1 |
| 13 | 1 |
| 14 | <1 |
| 15 | <0.1 |
| 16 | <1 |
| 17 | 0.6 |
| 18 | 0.8 |
| 19 | <1 |
| 20 | 0.2 |
| 21 | 0.1 |
| 22 | 0.3 |
| 23 | 0.2 |
| 24 | 0.2 |
| 25 | 0.6 |
| 26 | >1 |
| 30 | 0.3 |
| 31 | 0.2 |
| 32 | 0.4 |
| 34 | >10 |
| 36 | 0.2 |
| 37 | <1 |
| 38 | <1 |
| 39 | <1 |
| 40 | 1 |
| 43 | 0.9 |
| 44 | <1 |
| 49 | <1 |
| 50 | <1 |
| 51 | 0.6 |
| 52 | <0.1 |
| 53 | <1 |
| 54 | 1.3 |
| 56 | <0.1 |
| 58 | 0.1 |
| 59 | 0.3 |
| 62 | 6.4 |
| 63 | 4 |
| 67 | <1 |
| 68 | <1 |
| 69 | <1 |
| 70 | <1 |

TABLE 13-continued

IN VITRO MOUSE PERITONEAL MACROPHAGE LEUKOTRIENE C₄ INHIBITION

| Compound | IC$_{50}$ (μM) |
|---|---|
| 71 | <1 |
| 72 | <1 |
| 73 | <1 |
| 74 | <10 |
| 75 | <10 |
| 76 | <0.1 |
| 77 | <0.1 |
| 78 | <1 |
| 79 | <1 |
| 80 | <1 |
| 81 | <1 |
| 82 | <1 |
| 83 | <1 |

EXAMPLE 4

RAT EX VIVO LEUKOTRIENE B$_4$ INHIBITION

The test method described below measures the ability of a compound when administered orally to rats to inhibit the production of Leukotriene B$_4$ in their blood which is drawn and challenged.

Rats (CD, male, non-fasted, 250 g) are lightly anesthetized with carbon dioxide and an approximately 0.75 mL sample of whole blood is obtained via cardiac puncture. The sample is dispensed into 12×75 mm polypropylene tubes containing 8–10 μL of 10,000 units/mL heparin, mixed and then maintained on ice. The rats are allowed to recover approximately one hour then dosed orally with compound dissolved in PEG 400 at a 5 mL/Kg volume. Five (5) rats are utilized per group. Two (2) hours post dose the rats are again anesthetized with carbon dioxide and the blood sampled again via cardiac puncture.

Duplicate 200 μL portions of blood are added to 1.0 mL polypropylene tubes. A 10 μL portion of 1 mM A23187 Calcium Ionophore in dimethyl sulfoxide/Tris buffer is added to each tube. The tubes are gently vortexed then incubated in a 37° C. water bath for 30 minutes. The tubes are then centrifuged at 4000 rpm for 10 minutes. 50 μL portions of plasma are transferred to 1.0 mL tubes containing 200 μL of methanol. The tubes are vortexed then placed in the freezer overnight.

The tubes are removed from the freezer then centrifuged at 4000 rpm for 10 minutes. 20 μL portions of the methanol/plasma supernatant and 10 μL methanol dilutions of LTB$_4$ standard curve are transferred to 96 well v-bottom microtiter plates. The plates are vacuum dried at 40° C. A 40 μL portion of LTB$_4$ radioimmunoassay buffer is added to each well. The plate is bath sonicated for 5 minutes then assayed according to the manufacturer's (Advanced Magnetics; Cambridge, Mass.) instructions. Percent inhibition values are obtained by comparing the level of LTB$_4$ in the post-dose samples to the level in the pre-dose samples according to the equation below.

$$\% \text{ Inhibition} = \frac{(\text{LTB}_4 \text{ pre-dose}) - (\text{LTB}_4 \text{ post-dose})}{(\text{LTB}_4 \text{ pre-dose})} \times 100$$

A number of the compounds that are useful in the practice of the method of the invention were tested. The results are shown in Table 14 below.

TABLE 14

RAT EX VIVO LEUKOTRIENE B$_4$ INHIBITION

| Cpd | % I | Dose (mg/Kg) |
|---|---|---|
| 1 | 18 | 5 |
| 1 | 87 | 50 |
| 3 | 39 | 5 |
| 5 | 82 | 50 |
| 6 | 39 | 5 |
| 6 | 47 | 50 |
| 7 | 32 | 5 |
| 8 | 29 | 5 |
| 9 | 34 | 25 |
| 10 | 23 | 25 |
| 10 | 41 | 50 |
| 11 | 26 | 20 |
| 11 | 20 | 50 |
| 12 | 42 | 50 |
| 13 | 23 | 50 |
| 14 | 22 | 50 |
| 14 | 50 | 50 |
| 15 | 24 | 50 |
| 15 | 73 | 50 |
| 16 | 74 | 25 |
| 17 | 26 | 50 |
| 18 | 3 | 50 |
| 19 | 3 | 50 |
| 20 | 19 | 50 |
| 23 | 45 | 50 |
| 24 | 29 | 50 |
| 25 | 13 | 10 |
| 25 | 44 | 25 |
| 25 | 45 | 50 |
| 25 | 79 | 50 |
| 27 | 23 | 10 |
| 27 | 5 | 25 |
| 27 | 53 | 50 |
| 27 | 75 | 50 |
| 28 | 29 | 50 |
| 29 | 61 | 50 |
| 30 | 13 | 50 |
| 31 | 40 | 25 |
| 32 | 28 | 50 |
| 33 | 26 | 25 |
| 34 | −2.9 | 25 |
| 36 | 7 | 50 |
| 37 | 7 | 50 |
| 38 | 2 | 50 |
| 39 | 59 | 50 |
| 40 | 0 | 50 |
| 41 | 14 | 50 |
| 42 | 4 | 50 |
| 43 | 12 | 20 |
| 43 | 16 | 50 |
| 44 | 18 | 50 |
| 45 | 6 | 50 |
| 46 | 17 | 50 |
| 47 | 16 | 50 |
| 48 | 2 | 50 |
| 49 | 13 | 50 |
| 50 | 6 | 50 |
| 51 | 22 | 50 |
| 52 | 9 | 50 |
| 53 | 1 | 50 |
| 54 | 42 | 50 |
| 55 | 8 | 50 |
| 56 | 6 | 50 |
| 56 | 13 | 50 |
| 57 | 35 | 50 |
| 59 | 9 | 5 |
| 59 | 23 | 10 |
| 59 | 20 | 20 |
| 59 | 49 | 25 |
| 59 | 65 | 50 |
| 59 | 87 | 50 |
| 62 | 18 | 50 |
| 63 | 92 | 50 |
| 64 | 88 | 50 |

TABLE 14-continued

RAT EX VIVO LEUKOTRIENE B$_4$ INHIBITION

| Cpd | % I | Dose (mg/Kg) |
|---|---|---|
| 65 | 93 | 50 |
| 66 | 61 | 50 |
| 67 | 23 | 50 |
| 68 | 48 | 50 |
| 68 | 21 | 50 |
| 69 | 71 | 50 |
| 70 | 0 | 50 |
| 71 | 5 | 50 |
| 72 | 19 | 50 |
| 72 | 47 | 50 |
| 74 | 7 | 50 |
| 75 | 0 | 50 |
| 76 | 13 | 50 |
| 77 | 7 | 50 |
| 78 | 0 | 50 |

EXAMPLE 5

DOG EX VIVO LEUKOTRIENE B$_4$ INHIBITION

The test method described below measures the ability of a compound when administered orally to dogs to inhibit the production of Leukotriene B$_4$ (LTB$_4$) in their blood which is drawn and challenged at selected time points.

The test is conducted in beagle dogs (male and female; about 10 Kg). Prior to starting, the neck area of the beagle is shaved to allow easy access to the jugular vein. A 3–4 mL sample of blood is drawn from the jugular vein into a heparinized vacutainer. The dog is then dosed using a tube long enough to reach its stomach. The compound is dissolved in PEG 400 at a concentration such that the appropriate dose can be administered in approximately 5 mL. Immediately after the compound is given, a flush using 5 mL of vehicle is given to rinse the dosing tube. At selected time points following the dose, a 3–4 mL sample of blood is drawn.

The blood samples that have been drawn are challenged as soon as possible. A 0.5 mL portion of blood is aliquoted into 3 tubes (1 mL microtiter tubes). A 1 µL portion of 25 mM calcium ionophore in dimethyl sulfoxide is added to 2 of the tubes. A 1 µL portion of dimethyl sulfoxide is added to the third tube. The tubes are lightly mixed then placed in a 37° C. water bath for 30 minutes. The tubes are centrifuged at 11,000 rpm for 3 minutes and the plasma supernatant is transferred to clean tubes. A 50 µL portion of this plasma is added to a 1 mL microtiter tube containing 200 µL of methanol. The tubes are placed in the freezer at −20° C. for at least 1 hour then centrifuged at 2000 rpm for 10 minutes. A 10 µL portion of the methanol supernatant is dried under vacuum at ambient temperature and then reconstituted in LTB$_4$ buffer. The amount of LTB$_4$ in the sample is determined by radioimmunoassay performed according to the manufacturer's (Advanced Magnetics; Cambridge, Mass.) instructions. Percent inhibition values are obtained by comparing the level of LTB$_4$ in the post-dose sample to the level in the pre-dose sample according to the equation below.

$$\% \text{ Inhibition} = \frac{(\text{LTB}_4 \text{ predose}) - (\text{LTB}_4 \text{ postdose})}{(\text{LTB}_4 \text{ predose})} \times 100$$

A number of the compounds that are useful in the practice of the method of the invention were tested. The results are shown in Table 15 below where each entry represents the results from one dog. A negative number indicates stimulation of LTB$_4$ production. All compounds were tested at a dose of 5 mg/Kg.

TABLE 15

DOG EX VIVO LEUKOTRIENE B$_4$ INHIBITION

| Compound Number | % Inhibition | | | |
|---|---|---|---|---|
| | 1 hour | 2 hour | 4 hour | 6 hour |
| 1 | 100 | 100 | 100 | 93 |
| 1 | 100 | 100 | 100 | 95 |
| 3 | 100 | 100 | 83 | 51 |
| 3 | 100 | 99 | 95 | 84 |
| 5 | 100 | 100 | 99 | 20 |
| 5 | 100 | 75 | 44 | 50 |
| 6 | 100 | 62 | 27 | 19 |
| 6 | 86 | 11 | −36 | −52 |
| 7 | 100 | 100 | 70 | −21 |
| 7 | 100 | 99 | 56 | 48 |
| 8 | 100 | 92 | 27 | 9 |
| 8 | 100 | 100 | 11 | −32 |
| 9 | 100 | 34 | 33 | 56 |
| 9 | 100 | 83 | 18 | 54 |
| 10 | 100 | 100 | 49 | 52 |
| 10 | 100 | 100 | 34 | 42 |
| 11 | 100 | 100 | 77 | −17 |
| 11 | 100 | 100 | 41 | 30 |
| 15 | 100 | 99 | 98 | 100 |
| 15 | 99 | 100 | 99 | 100 |
| 15 | 95 | 100 | 96 | 84 |
| 15 | 100 | 98 | 31 | 14 |
| 16 | 100 | 97 | −8 | −39 |
| 16 | 100 | 100 | −18 | −24 |
| 16 | 100 | 100 | −14 | −186 |
| 16 | 100 | 100 | −80 | −204 |
| 17 | 100 | 98 | 98 | 64 |
| 17 | 100 | 100 | 70 | 43 |
| 18 | 100 | 100 | 49 | 46 |
| 18 | 100 | 100 | 57 | −12 |
| 19 | 100 | 84 | 11 | 29 |
| 19 | 100 | 100 | 74 | 65 |
| 20 | 100 | 100 | 57 | 17 |
| 20 | 100 | 100 | 64 | 13 |
| 21 | 100 | 95 | 0 | 24 |
| 21 | 100 | 88 | −37 | −8 |
| 22 | 100 | 78 | −401 | −518 |
| 22 | 100 | −140 | −381 | −421 |
| 23 | 100 | 99 | 84 | 15 |
| 23 | 99 | 99 | 82 | 80 |
| 23 | 100 | 100 | 100 | 98 |
| 23 | 100 | 100 | 59 | 56 |
| 24 | 99 | 73 | 7 | −21 |
| 24 | 100 | 84 | 14 | −24 |
| 25 | 100 | 51 | −45 | 7 |
| 25 | 98 | 57 | −78 | 9 |
| 42 | 99 | 99 | 97 | 78 |
| 42 | 98 | 100 | 100 | 85 |
| 42 | 100 | 100 | 100 | 91 |
| 42 | 100 | 100 | −91 | −150 |
| 44 | 80 | 11 | −19 | −19 |
| 44 | 52 | 5 | 12 | 30 |
| 46 | 80 | 64 | 11 | −23 |
| 46 | 77 | 58 | 2 | 46 |
| 54 | 99 | 97 | 33 | 43 |
| 58 | 1 | −21 | −43 | 8 |
| 58 | −24 | −35 | −63 | −34 |
| 59 | 100 | 99 | 83 | 37 |
| 59 | 100 | 100 | 75 | 55 |
| 59 | 100 | 100 | 100 | 93 |
| 59 | 100 | 100 | 78 | 76 |
| 60 | 100 | 100 | −79 | −95 |
| 60 | 97 | 52 | 49 | 76 |
| 61 | 100 | 100 | 29 | −32 |
| 61 | 100 | 99 | −2 | 22 |

The claimed invention is:
1. A method of inhibiting leukotriene biosynthesis in an animal and of treating in an animal a condition responsive to such inhibition comprising administering to the animal, in an amount effective to inhibit leukotriene biosynthesis, a compound of the formula:

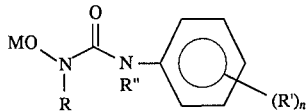

wherein n is 0, 1, 2 or 3,

R is selected from the group consisting of hydrogen; cyclic alkyl containing five to ten carbon atoms; straight chain or branched chain alkyl containing one to fourteen carbon atoms and substituted straight chain or branched chain alkyl containing one to twelve carbon atoms, wherein the substituent is alkoxycarbonyl wherein the alkoxy group contains one to four carbon atoms; alkoxyalkyl wherein the alkoxy moiety contains one to six carbon atoms and the alkyl moiety contains one to six atoms;

each R' is independently selected from the group consisting of halogen; nitro; straight chain or branched chain alkyl containing one to five carbon atoms; alkoxy containing one to four carbon atoms; alkoxyphenyl wherein the alkoxy group contains one to eight carbon atoms; alkylthio containing one to four carbon atoms; alkylsulfonoxy containing one to four carbon atoms; alkylsulfinyl containing one to four carbon atoms; alkylsulfonyl containing one to four carbon atoms; benzoyl; benzyl; cyclohexylmethoxy; cyclopentyloxy; phenoxy; phenyl; phenylalkyloxy wherein the alkyl group contains one to four carbon atoms; trifluoromethyl; trifluoromethylthio; and trifluoromethylsulfonoxy;

R" is selected from the group consisting of hydrogen and straight chain alkyl containing one to twelve carbon atoms; and M is selected from the group consisting of hydrogen, a pharmaceutically acceptable cation, and a pharmaceutically acceptable metabolically cleavable group with the proviso that R, R', and R" are not all hydrogen.

2. A method according to claim 1, wherein R is selected from the group consisting of straight chain or branched chain alkyl containing one to six carbon atoms.

3. A method according to claim 2, wherein R is selected from the group consisting of methyl, 1-methylethyl, 1-ethylpropyl, and 1-methylpropyl.

4. A method according to claim 1, wherein R is selected from the group consisting of cycloalkyl of five to eight carbon atoms.

5. A method according to claim 1, wherein R' is selected from the group consisting of halogen, nitro, straight chain alkyl containing one to four carbon atoms, alkylthio containing one to four atoms, and phenoxy.

6. A method according to claim 1, wherein R' is selected from the group consisting of methylthio, methylsulfinyl and methylsulfonyl.

7. A method according to claim 1, wherein n is 1.

8. A method according to claim 7, wherein R' is located in the para position on the phenyl ring.

9. A method according to claim 7, wherein R' is located in the meta position of the phenyl ring.

10. A method according to claim 1, wherein n is 2.

11. A method according to claim 1, wherein n is 0.

12. A method according to claim 1, wherein M is hydrogen.

13. A method according to claim 1, wherein R" is hydrogen.

14. A method according to claim 1, wherein the compound is selected from the group consisting of:
1-hydroxy-1-methyl-3-[3-(trifluoromethylsulfonoxy)phenyl]urea,
1-hydroxy-1-methyl-3-[3-(methylthio)phenyl]urea,
1-hydroxy-1-methyl-3-[3-(trifluoromethylthio)phenyl]urea,
1-hydroxy-3-(3-methoxyphenyl)-1-methylurea,
3-(3-bromophenyl)-1-hydroxy-1-methylurea,
1-hydroxy-1-methyl-3-(3-methylphenyl)urea,
3-(3-fluorophenyl)-1-hydroxy-1-methylurea,
1-hydroxy-1-methyl-3-(3-nitrophenyl)urea,
1-hydroxy-1-methyl-3-phenylurea,
3-(4-fluorophenyl)-1-hydroxy-1-methylurea,
3-(4-butylphenyl)-1-hydroxy-1-methylurea,
1-hydroxy-1-methyl-3-(4-nitrophenyl)urea,
1-hydroxy-1-methyl-3-(4-phenoxyphenyl)urea,
1-hydroxy-1-(1-methylethyl)-3-[3-(methylthio)phenyl]urea,
1-hydroxy-1-(1-methylethyl)-3-phenylurea,
3-(4-fluorophenyl)-1-hydroxy-1-(1-methylethyl)urea,
3-(4-bromophenyl)-1-hydroxy-1-(1-methylethyl)urea,
3-(2-fluorophenyl)-1-hydroxy-1-(1-methylethyl)urea,
1-hydroxy-1-(1-methylethyl)-3-(3-methylphenyl)urea,
1-hydroxy-3-(3-methoxyphenyl)-1-(1-methylethyl)urea,
1-hydroxy-3-(4-methoxyphenyl)-1-(1-methylethyl)urea,
3-(2-chlorophenyl)-1-hydroxy-1-(1-methylethyl)urea,
1-hydroxy-1-(1-methylethyl)-3-(2-methylphenyl)urea,
3-(2,6-dimethylphenyl)-1-hydroxy-1-(1-methylethyl)urea,
3-(4-butylphenyl)-1-hydroxy-1-(1-methylethyl)urea,
3-(2,5-dimethoxyphenyl)-1-hydroxy-1-(1-methylethyl)urea,
1-hydroxy-3-(2-methoxyphenyl)-1-(1-methylethyl)urea,
1-hydroxy-1-(1-methylethyl)-3-(4-nitrophenyl)urea,
1-cyclohexyl-1-hydroxy-3-[4-(methylthio)phenyl]urea,
1-cyclohexyl-1-hydroxy-3-[3-(methylthio)phenyl]urea,
1-hydroxy-3-(3-methoxyphenyl)urea,
1-hydroxy-3-[3-(methylthio)phenyl]urea,
1-cyclooctyl-1-hydroxy-3-phenylurea,
1-cyclooctyl-1-hydroxy-3-(4-methoxyphenyl)urea,
1-cyclooctyl-1-hydroxy-3-(4-nitrophenyl)urea,
1-(1-ethylpropyl)-1-hydroxy-3-[4-(methylthio)phenyl]urea,
1-(1-ethylpropyl)-1-hydroxy-3-(4-nitrophenyl)urea,
3-(4-bromophenyl)-1-(1-ethylpropyl)-1-hydroxyurea,
1-ethyl-1-hydroxy-3-phenylurea,
1-hydroxy-1-(3-methylbutyl)-3-phenylurea,
1-(2-ethoxyethyl)-1-hydroxy-3-phenylurea,
1-cyclopentyl-1-hydroxy-3-phenylurea,
1-(2-ethylhexyl)-1-hydroxy-3-phenylurea,
1-(3,3-dimethylbutyl)-1-hydroxy-3-phenylurea,
1-hydroxy-3-phenyl-1-(3,5,5-trimethylhexyl)urea,
6-(1-hydroxy-3-phenylureido)-1-hexanoic acid ethyl ester,
1-cycloheptyl-1-hydroxy-3-phenylurea,
1-hydroxy-1-octyl-3-phenylurea,
1-dodecyl-1-hydroxy-3-phenylurea,
1-hydroxy-1-(2-methylpropyl)-3-phenylurea,
1-hydroxy-3-phenyl-1-propylurea,
1-hydroxy-1-pentyl-3-phenylurea,
3-(4-butylphenyl)-1-hydroxy-1-pentylurea,
1-hydroxy-1-(2-methylpropyl)-3-[3-(methylthio)phenyl] urea,
1-hydroxy-1-methyl-3-[3-(methylsulfonyl)phenyl]urea,
1-hydroxy-1-(1-methylethyl)-3-[3-(methylsulfonyl)phenyl] urea,
1-hydroxy-1-(1-methylethyl)-3-[3-(methylsulfinyl)phenyl] urea, 1-hydroxy-1-(1-methylethyl)-3-[4-(methylsulfonyl)phenyl] urea,
1-hydroxy-1-(1-methylethyl)-3-[4-(methylsulfinyl)phenyl] urea,
1-hydroxy-1-methyl-3-[4-(methylsulfinyl)phenyl]urea,
1-hydroxy-1-methyl-3-[4-(methylsulfonyl)phenyl]urea,
1-hydroxy-1-(1-methylethyl)-3-(3,4,5-trimethoxyphenyl) urea, and
1-hydroxy-1-(1-methylethyl)-3-(2,4, 5-trimethylphenyl) urea.

15. A method according to claim 1, wherein the compound is selected from the group consisting of:
1-hydroxy-1-(1-methylbutyl)-3-phenylurea,
1-hydroxy-1-(1-methylpropyl)-3-phenylurea,
1-hydroxy-1-(1-propylbutyl)-3-phenylurea,
1-hydroxy-1-(1-ethylbutyl)-3-phenylurea,
1-hydroxy-1-(1-ethylpropyl)-3-(4-phenoxyphenyl)urea,
1-hydroxy-1-(1-ethylpropyl)-3-(3,5-bis(trifluoromethyl)phenyl)urea,
1-hydroxy-1-(1-ethylpropyl)-3-methyl-3-phenylurea,
1-hydroxy-1,3-dimethyl-3-phenylurea,
1-hydroxy-1-(1-ethylpropyl)-3-(2-phenoxyphenyl)urea,
1-hydroxy-1-(1-ethylpropyl)-3-(3-phenoxyphenyl)urea,
1-hydroxy-1-(1-ethylpropyl)-3-(4-benzylphenyl)urea,
1-hydroxy-1-(1-ethylpropyl)-3-(4-benzoylphenyl)urea,
1-hydroxy-1-(1-ethylpropyl)-3-(4-benzyloxyphenyl)urea,
1-hydroxy-1-(1-ethylpropyl)-3-[4-(cyclohexylmethoxy)phenyl]urea,
1-hydroxy-1-(1-ethylpropyl)-3-[4-(3-phenylptopyloxy)phenyl]urea,
1-hydroxy-1-(1-ethylpropyl)-3-(biphenyl-4-yl)urea,
1-hydroxy-1-(1-ethylpropyl)-3-(3-cyclopentyloxy-4-methoxyphenyl)urea, and
1-hydroxy-1-(1-ethylpropyl)-3-(4'-octyloxybiphenyl-4-yl)urea.

16. A method according to claim 1, wherein the compound is 1-hydroxy-1-methyl-3-[4-(methylthio)phenyl] urea.

17. A method according to claim 1, wherein the compound is 1-hydroxy-1-(1-methylethyl)-3-[4-(methylthio)phenyl]urea.

18. A method according to claim 1, wherein the compound is 1-(1-ethylpropyl)-1-hydroxy-3-phenylurea.

19. A method according to claim 1, wherein the compound is 1-(1-ethylpropyl)-1-hydroxy-3-(4-methylthio)phenylurea.

20. A method according to claim 1, wherein the compound is 1-hydroxy-1-(1-ethylpropyl)-3-(4-phenoxyphenyl) urea.

21. A method according to claim 1, wherein the compound is 1-hydroxy-1-(1-ethylpropyl)-3-(2-phenoxyphenyl) urea.

22. A method according to claim 1, wherein the compound is 1-hydroxy-1-(1-methylethyl)-3-(4-butylphenyl) urea.

23. A method according to claim 1, wherein the compound is 1-hydroxy-1-(-1methylpropyl)-3-phenylurea.

24. A method according to claim 1, wherein the compound is 1-hydroxy-1-(1-ethylpropyl)-3-(3-phenoxyphenyl) urea.

25. A method according to claim 1, wherein the compound is 1-hydroxy-1-methyl-3-(4-phenoxyphenyl)urea.

26. A method according to claim 1, wherein the condition responsive to leukotriene biosynthesis inhibition is selected from the group consisting of arthritis, rheumatoid arthritis, osteoarthritis, allergic rhinitis, psoriasis, dermatitis, ischemic induced myocardial injury, reperfusion injury, gout, asthma, adult respiratory distress syndrome, atherosclerosis, inflammatory bowel disease, stroke, psoriasis, spinal cord injury, and traumatic brain injury.

27. A method according to claim 1, wherein the condition responsive to leukotriene biosynthesis inhibition is an inflammatory disease.

28. A method according to claim 1, wherein the condition responsive to leukotriene biosynthesis inhibition is asthma.

29. A pharmaceutical composition for treating a condition responsive to inhibition of leukotriene biosynthesis, comprising
(i) a pharmaceutically acceptable vehicle; and
(ii) a compound of the formula:

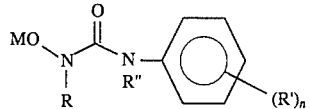

wherein n is 0, 1, 2 or 3,
R is selected from the group consisting of hydrogen; cyclic alkyl containing five to ten carbon atoms; straight chain or branched chain alkyl containing one to fourteen carbon atoms and substituted straight chain or branched chain alkyl containing one to twelve carbon atoms, wherein the substituent is alkoxycarbonyl wherein the alkoxy group contains one to four carbon atoms; alkoxyalkyl wherein the alkoxy moiety contains one to six carbon atoms and the alkyl moiety contains one to six atoms;

each R' is independently selected from the group consisting of halogen; nitro; straight chain or branched chain alkyl containing one to five carbon atoms; alkoxy containing one to four carbon atoms; alkoxyphenyl wherein the alkoxy group contains one to eight carbon atoms; alkylthio containing one to four carbon atoms; alkylsulfonoxy containing one to four carbon atoms; alkylsulfinyl containing one to four carbon atoms; alkylsulfonyl containing one to four carbon atoms; benzoyl; benzyl; cyclohexylmethoxy; cyclopentyloxy; phenoxy; phenyl; phenylalkyloxy wherein the alkyl group contains one to four carbon atoms; trifluoromethyl; trifluoromethylthio; and trifluoromethylsulfonoxy;

R" is selected from the group consisting of hydrogen and straight chain alkyl containing one to twelve carbon atoms; and M is selected from the group consisting of hydrogen, a pharmaceutically acceptable cation, and a pharmaceutically acceptable metabolically cleavable group with the proviso that R, R', and R" are not all hydrogen, in an amount effective to inhibit leukotriene biosynthesis.

30. A pharmaceutical composition according to claim 29, suitable for oral administration and comprising one or more ingredients selected from the group consisting of diluents, binders, lubricants, disintegrants, coloring agents, and flavoring agents.

* * * * *

UNITED STATES PATENT AND TRADEMARK OFFICE
CERTIFICATE OF CORRECTION

PATENT NO. : 5,612,377
DATED : March 18, 1998
INVENTOR(S) : Stephen L. Crooks, et al.

It is certified that error appears in the above-identified patent and that said Letters Patent is hereby corrected as shown below:

Column 43, line 9, "(2,4, 5-trimethylphenyl)" should be --(2,4,5-trimethylphenyl--;

Column 43, line 26, "(cy clohexylmethoxy" should be --cyclohexylmethoxy--; and

Column 43, line 28, "(3-phenylptopyloxy)" should be --(3-phenylpropyloxy)--.

Signed and Sealed this

Twenty-seventh Day of October, 1998

Attest:

BRUCE LEHMAN

*Attesting Officer*    *Commissioner of Patents and Trademarks*